United States Patent
Shim et al.

(10) Patent No.: US 10,576,619 B2
(45) Date of Patent: Mar. 3, 2020

(54) ASSISTING TORQUE SETTING METHOD AND APPARATUS

(71) Applicant: Samsung Electronics Co., Ltd., Suwon-si, Gyeonggi-do (KR)

(72) Inventors: Youngbo Shim, Seoul (KR); Sunghwan Ahn, Seoul (KR); Seungyong Hyung, Yongin-si (KR); Youngjin Park, Seoul (KR); Keehong Seo, Seoul (KR); Bokman Lim, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 1085 days.

(21) Appl. No.: 14/873,696

(22) Filed: Oct. 2, 2015

(65) Prior Publication Data

US 2016/0184985 A1    Jun. 30, 2016

(30) Foreign Application Priority Data

Dec. 26, 2014  (KR) .................. 10-2014-0190782
Sep. 21, 2015  (KR) .................. 10-2015-0133395

(51) Int. Cl.
*A61H 3/00*     (2006.01)
*B25J 9/00*     (2006.01)
(Continued)

(52) U.S. Cl.
CPC ............... *B25J 9/0006* (2013.01); *A61F 2/70* (2013.01); *A61H 3/00* (2013.01); *B25J 9/1671* (2013.01);
(Continued)

(58) Field of Classification Search
CPC ......... B25J 9/0006; B25J 9/1671; A61H 3/00; A61H 2230/045; A61H 2230/625;
(Continued)

(56) References Cited

U.S. PATENT DOCUMENTS 7,537,573 B2 *  5/2009  Horst ................... A61H 1/0237
                                                        482/5
7,857,774 B2    12/2010  Sankai
(Continued)

FOREIGN PATENT DOCUMENTS

CN   101184462 A   5/2008
CN   101242879 A   8/2008
(Continued)

OTHER PUBLICATIONS

Extended European Search Report issued by the European Patent Office dated May 27, 2016 for the corresponding EP Patent Application No. 15196813.8.
(Continued)

*Primary Examiner* — Timothy A Stanis
(74) *Attorney, Agent, or Firm* — Harness, Dickey and Pierce, P.L.C.

(57) ABSTRACT

Provided is an assisting torque setting apparatus and method, wherein the apparatus is configured to calculate an evaluation value of at least one index based on gait data of a user, set a stable assisting torque based on the evaluation value, set a basic assisting torque corresponding to a gait motion of the user based on the gait data, and set a final assisting torque based on the stable assisting torque and the basic assisting torque.

35 Claims, 18 Drawing Sheets

(51) Int. Cl.
  *A61F 2/70* (2006.01)
  *B25J 9/16* (2006.01)
(52) U.S. Cl.
  CPC ... *A61F 2002/701* (2013.01); *A61F 2002/704* (2013.01); *A61H 2003/007* (2013.01); *Y10S 901/46* (2013.01)
(58) Field of Classification Search
  CPC ........ A61H 2230/105; A61H 2201/165; A61H 2003/007
  See application file for complete search history.

(56) References Cited

U.S. PATENT DOCUMENTS

| | | | | |
|---|---|---|---|---|
| 8,181,520 | B2* | 5/2012 | Kadota | A61B 5/1071 601/33 |
| 9,216,131 | B2* | 12/2015 | Nakashima | A61H 3/00 |
| 2004/0158175 | A1* | 8/2004 | Ikeuchi | A61H 3/008 601/5 |
| 2010/0049102 | A1 | 2/2010 | Yasuhara | |
| 2011/0004322 | A1 | 1/2011 | Sankai | |
| 2014/0121575 | A1 | 5/2014 | Yasuhara et al. | |

FOREIGN PATENT DOCUMENTS

| | | |
|---|---|---|
| CN | 102139714 A | 8/2011 |
| EP | 1932567 A1 | 6/2008 |
| JP | 2010017464 A | 1/2010 |
| JP | 2010063813 A | 3/2010 |
| JP | 2010104397 A | 5/2010 |
| JP | 2011-239887 A | 12/2011 |
| JP | 2012110497 A | 6/2012 |
| JP | 2012-245212 A | 12/2012 |
| JP | 2013000296 A | 1/2013 |
| JP | 2013111368 A | 6/2013 |
| KR | 20080099752 A | 11/2008 |
| KR | 20080102466 A | 11/2008 |
| KR | 20120064571 A | 6/2012 |
| KR | 20120072249 A | 7/2012 |
| KR | 20130112158 A | 10/2013 |
| KR | 20140005415 A | 1/2014 |
| WO | WO-2011/049171 A1 | 4/2011 |
| WO | WO-2013-188868 A1 | 12/2013 |

OTHER PUBLICATIONS

Office Action issued by the Chinese Patent Office dated Jun. 5, 2018 for CN Patent Application No. 201511001265.4.
Japanese Office Action dated Jun. 14, 2019 for JP Patent Application No. 2015-241191 (with English translation).

* cited by examiner

ASSISTING TORQUE SETTING METHOD AND APPARATUS

CROSS-REFERENCE TO RELATED APPLICATION

[1] This application claims the priority benefit of Korean Patent Applications No. 10-2014-0190782, filed on Dec. 26, 2014, and No. 10-2015-0133395, filed on Sep. 21, 2015 in the Korean Intellectual Property Office, the entire contents of both of which are incorporated herein by reference in their entirety.

BACKGROUND

1. Field

Example embodiments relate to an assisting torque setting method and/or an apparatus configured to perform the same.

2. Description of the Related Art

With the onset of rapidly aging societies, many people may be experiencing inconvenience and pain from joint problems. Therefore, there may be increased interest in walking assistance apparatuses enabling the elderly or patients with joint problems to walk with less effort. Furthermore, walking assistance apparatuses for intensifying muscular strength of human bodies may be useful for military purposes.

In general, walking assistance apparatuses may include body frames disposed on trunks of users, pelvic frames coupled to lower sides of the body frames to cover pelvises of the users, femoral frames disposed on thighs of the users, sural frames disposed on calves of the users, and pedial frames disposed on feet of the users. The pelvic frames and femoral frames may be connected rotatably by hip joint portions, the femoral frames and sural frames may be connected rotatably by knee joint portions, and/or the sural frames and pedial frames may be connected rotatably by ankle joint portions.

SUMMARY

Some example embodiments relate to an assisting torque setting apparatus.

In some example embodiments, the apparatus may include a gait data receiver configured to receive gait data of a user, a stable assisting torque setter configured to set a stable assisting torque using an evaluation value of at least one index calculated based on the gait data, a basic assisting torque setter configured to set a basic assisting torque corresponding to a gait motion of the user based on the gait data, and a final assisting torque setter configured to set a final assisting torque based on the stable assisting torque and the basic assisting torque.

The stable assisting torque setter may include an index evaluator configured to calculate the evaluation value of the at least one index based on the gait data, a weight calculator configured to calculate a weight of the at least one index based on a difference between the evaluation value and a threshold corresponding to the at least one index, and a stable assisting torque calculator configured to calculate the stable assisting torque by applying the weight to an initial stable assisting torque corresponding to the at least one index.

The at least one index may include at least one of a gait symmetry indicating a degree of symmetry between both legs of the user, a stride length of the user, a stride width of the user, a foot clearance indicating a space between a ground and a foot of the user, a landing speed indicating a speed of the foot descending to the ground, and a walk ratio.

The index evaluator may be configured to classify the gait data based on a stride, and calculate the evaluation value of the at least one index based on the classified gait data.

The index evaluator may be configured to compare the evaluation value to a predetermined threshold, and determine whether a gait of the user is stable based on the at least one index.

The index evaluator may be configured to estimate a similarity between a trajectory of a left hip-joint angle and a trajectory of a right hip-joint angle of the user in the gait data, and determine the similarity as an evaluation value of the gait symmetry.

The index evaluator may be configured to estimate the similarity between the trajectory of the left hip-joint angle and the trajectory of the right hip-joint angle of the user based on a dynamic time warping (DTW).

The index evaluator may be configured to estimate, with respect to a plurality of strides, an average stride length by calculating an average of a left hip-joint angle range and a right hip-joint angle range in the gait data, and determine the average stride length as an evaluation value of the stride length.

The index evaluator may be configured to extract, with respect to a plurality of strides, a maximum flexion angle of a left hip-joint and a maximum flexion angle of a right hip-joint from the gait data, and determine the maximum flexion angle of the left hip-joint and the maximum flexion angle of the right hip-joint as an evaluation value of the foot clearance.

The weight calculator may be configured to calculate the weight by normalizing the difference between the evaluation value and the threshold.

The weight calculator may be configured to set "0" as a weight of an index for which the index evaluator determines that the gait of the user is stable.

The stable assisting torque calculator may be configured to set the initial stable assisting torque based on the gait data.

The stable assisting torque calculator may be configured to set the initial stable assisting torque for the gait symmetry based on a difference between a trajectory of a left hip-joint angle and a trajectory of a right hip-joint angle in the gait data.

The stable assisting torque calculator may be configured to extract an intersecting point in time at which a left leg and a right leg of the user intersect, based on the trajectory of the left hip-joint angle and the trajectory of the right hip-joint angle in the gait data, and set a peak torque of a predetermined period of time from the intersecting point in time as the initial stable assisting torque of the stride length.

The stable assisting torque calculator may be configured to extract a point in time at which a swinging leg of the user approaches a ground, based on the trajectory of the left hip-joint angle and the trajectory of the right hip-joint angle in the gait data, and set a peak torque of a predetermined period of time from the extracted point in time as the initial stable assisting torque of the foot clearance.

The assisting torque setting apparatus may further include a gait motion recognizer configured to recognize the gait motion of the user based on the gait data, wherein the basic assisting torque setter may be configured to set the basic assisting torque as "0" in response to the gait motion recognizer recognizing that the user does not perform the gait motion.

The basic assisting torque setter may be configured to estimate a periodicity of the gait motion of the user by applying the gait data to an adaptive oscillator (AO), and set an assisting torque corresponding to the estimated periodicity as the basic assisting torque.

The basic torque assisting torque may be configured to model the gait motion of the user to be in a plurality of states, recognize a gait state corresponding to the gait motion of the user among the modeled gait states by applying the gait data to a finite state machine (FSM), and set an assisting torque obtained based on the recognized gait state as the basic assisting torque.

The final assisting torque setter may be configured to set the final assisting torque by combining the stable assisting torque and the basic assisting torque.

The final assisting torque setter may be configured to set a value having a greater absolute value between the stable assisting torque and the basic assisting torque, as the final assisting torque.

Other example embodiments relate to an assisting torque setting apparatus.

In some example embodiments, the assisting torque setting apparatus may include an index evaluator configured to calculate an evaluation value of at least one index indicating a gait stability of a user based on gait data of the user, a weight calculator configured to calculate a weight of the at least one index based on a difference between the evaluation value and a threshold corresponding to the at least one index, and an assisting torque setter configured to set a stable assisting torque by applying the weight to an initial stable assisting torque corresponding to the at least one index.

The stable assisting torque setter may be configured to set the initial stable assisting torque based on the gait data.

The assisting torque setting apparatus may further include a basic assisting torque setter configured to set a basic assisting torque corresponding to a gait motion of the user based on the gait data, wherein the assisting torque setter may be configured to set a final assisting torque based on the basic assisting torque and the stable assisting torque.

Other example embodiments relate to a walking assistance apparatus.

In some example embodiments, the walking assistance apparatus may include a gait data receiver configured to receive gait data of a user, a stable assisting torque configured to calculate an evaluation value of at least one index based on the gait data, and set a stable assisting torque based on the evaluation value, a basic assisting torque configured to set a basic assisting torque corresponding to a gait motion of the user based on the gait data, a final assisting torque setter configured to set a final assisting torque based on the stable assisting torque and the basic assisting torque, and a driving controller configured to control driving of the walking assistance apparatus based on the final assisting torque.

Other example embodiments relate to an assisting torque setting method.

In some example embodiments, the assisting torque setting method may include receiving gait data of a user, calculating an evaluation value of at least one index based on the gait data and setting a stable assisting torque based on the evaluation value, setting a basic assisting torque corresponding to a gait motion of the user based on the gait data, and setting a final assisting torque based on the stable assisting torque and the basic assisting torque.

Other example embodiments relate to an assisting torque setting method.

In some example embodiments, the assisting torque setting method may include calculating an evaluation value of at least one index indicating a gait stability of a user based on gait data of the user, calculating a weight of the at least one index based on a difference between the evaluation value and a threshold corresponding to the at least one index, and setting a stable assisting torque by applying the weight to an initial stable assisting torque corresponding to the at least one index.

Other example embodiments relate to a walking assistance method.

In some example embodiments, the walking assistance method may include receiving gait data of a user, calculating an evaluation value of at least one index based on the gait data and setting a stable assisting torque based on the evaluation value, setting a basic assisting torque corresponding to a gait motion of the user based on the gait data, setting a final assisting torque based on the stable assisting torque and the basic assisting torque, and controlling driving of a walking assistance apparatus based on the final assisting torque.

Other example embodiments relate to a walking assistance apparatus.

In some example embodiments, the walking assistance apparatus includes an assistance device configured to be worn on legs of a user; a driver configured to output a final assistance torque to drive the assistance device; and a controller.

In some example embodiments, the controller may be configured to determine the final assistance torque by, determining a basic assistance torque based on a gait motion of the user, determining a stable assistance torque based on evaluation values, and determining the final assistance torque based on one or more of the stable assisting torque and the basic assisting torque.

In some example embodiments, the basic assistance torque is not a function of the evaluation values.

In some example embodiments, the walking assistance apparatus may further include one or more sensors configured to detect information associated with the gait motion of the user.

In some example embodiments, the gait motion is one of a step of one of the legs of the user and a stride of the legs of the user.

In some example embodiments, the information includes information on one or more of angles of hip joints of the user, a moving direction of the hip joints of the user.

In some example embodiments, the controller is configured to, evaluate the gait motion to generate the evaluation values by determining one or more of a symmetry between the gait motion of a right leg of the user and the gait motion of a left leg of the user, a length of a stride included in the gait motion, a width of the stride, a clearance between a foot of the user and a ground, a speed in which the foot of the user contacts the ground, and a number of strides in the gait motion in a period of time, and determine whether the gait motion is stable based on whether the evaluation values less than or equal to threshold values associated therewith.

In some example embodiments, the controller is configured to set the basic assistance torque as the final assistance torque, if the controller determines that the gait motion is stable.

In some example embodiments, the controller is configured to, correct a difference between trajectories of the legs of the user based on the initial assistance torque associated with the symmetry, and set a time period in which the initial assistance torque is provided to each of the legs of the user based on the length of the stride, and set the peak torque associated with the initial assistance torque based on a time at which the clearance is smallest.

In some example embodiments, the controller is configured to, determine a weight given to the evaluation values based on a difference between each of the evaluation values and a respective one of the threshold values associated therewith.

In some example embodiments, the weight given to each of the evaluation values increases as the difference between the evaluation value and the respective one of the threshold value increases.

In some example embodiments, the controller is configured to, determine the stable assistance torque by applying the weight to initial assistance torques associated with each of the evaluation values.

In some example embodiments, the controller is configured to determine the basic assistance torque by applying the gait motion to one of an adaptive oscillator and a finite state machine.

In some example embodiments, the controller is configured to determine the basic assistance torque using the adaptive oscillator by estimating a pattern of the gait motion.

In some example embodiments, the controller is configured to determine the basic assistance torque using the finite state machine by determining which of a plurality of gait states associated with the finite state machine correspond to the gait motion.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1A:
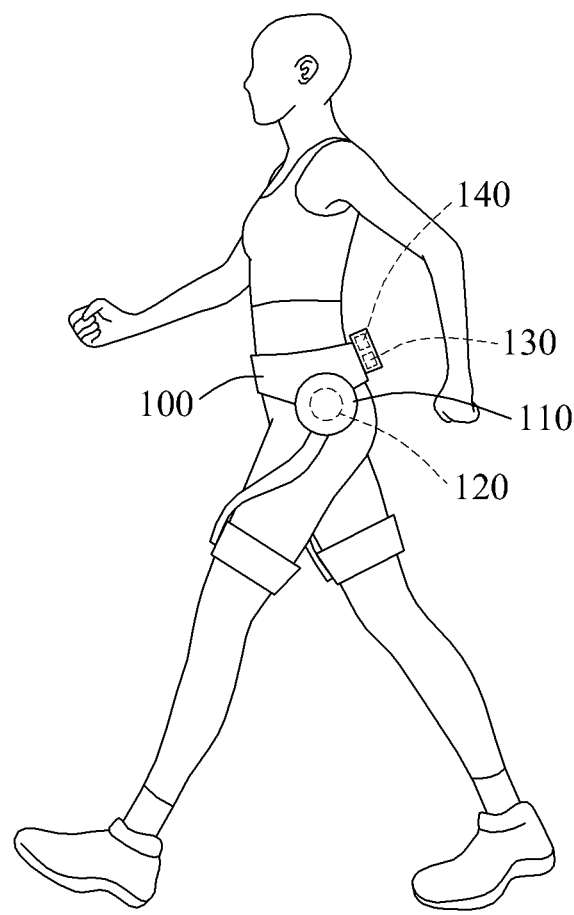
FIGS. 1A and 1B illustrate examples of a walking assistance apparatus according to example embodiments.

Hereinafter, some example embodiments will be described in detail with reference to the accompanying drawings.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "include" and/or "have," when used in this specification, specify the presence of stated features, integers, steps, operations, elements, components or combinations thereof, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 1B:
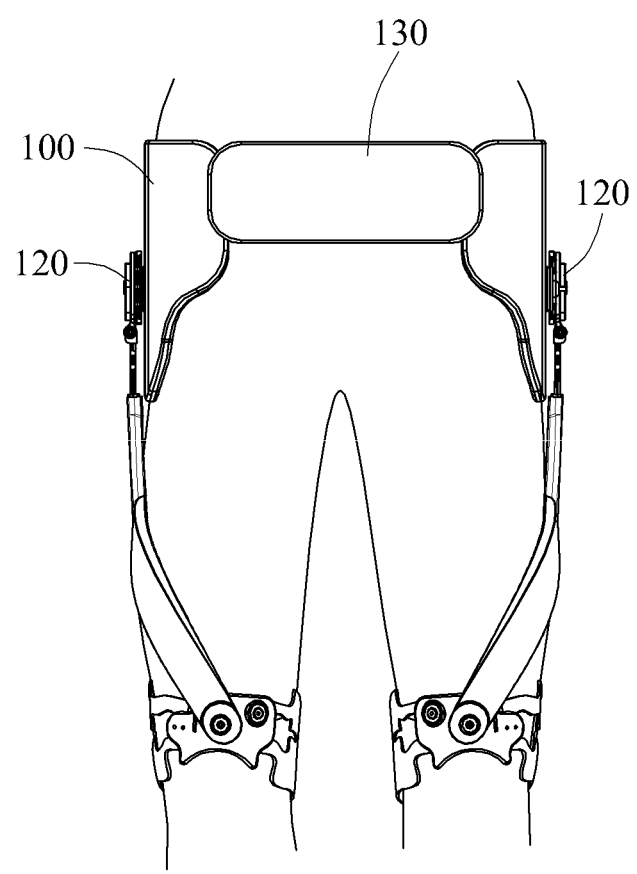

FIGS. 1A and 1B illustrate examples of a walking assistance apparatus according to example embodiments.

Referring to FIGS. 1A and 1B, a walking assistance apparatus 100 may be mounted on a user to assist a gait of the user. The waking assistance apparatus 100 includes a driving portion 110, a sensor portion 120, an inertial measurement unit (IMU) sensor 130, and a controller 140.

Although FIGS. 1A and 1B illustrate a hip-type walking assistance apparatus, the type of the walking assistance apparatus is not limited thereto. The walking assistance apparatus may be applicable to, for example, a walking assistance apparatus that supports an entire pelvic limb, a walking assistance apparatus that supports a portion of a pelvic limb, etc. The walking assistance apparatus that supports a portion of a pelvic limb may be applicable to, for example, a walking assistance apparatus providing support up to a knee, and a walking assistance apparatus providing support up to an ankle.

The driving portion 110 may be disposed on each of a left hip portion and a right hip portion of a user to drive both hip joints of the user.

The sensor portion 120 may be disposed on each of the left and right hip portions and measure hip joint angle information of the user while the user is walking. The hip joint angle information sensed by the sensor portion 120 may include the angle of each hip joint, a difference between the angles of both hip joints, and the motion direction of each hip joint. In an example, the sensor portion 120 may be disposed internally to the driving portion 110.

In another example, the sensor portion 120 may include a potentiometer. The potentiometer may sense at least one of variations of R-axial and L-axial joint angular velocities and variations of R-axial and L-axial joint angles based on a gait motion of the user.

The IMU sensor 130 may measure acceleration information and posture information while the user is walking. For example, the IMU sensor 130 may sense at least one of variations of X-axial, Y-axial, and Z-axial angular velocities and variations of X-axial, Y-axial, and Z-axial accelerations based on the gait motion of the user. The walking assistance apparatus 100 may detect a landing point in time of a foot of the user based on the acceleration information measured by the IMU sensor 130. When a sensor, for example, a pressure sensor and a force sensor, configured to detect a landing point in time of a foot is included in the sensing portion 120, the walking assistance apparatus 100 may detect the landing point of the foot of the user using the sensor.

Also, the walking assistance apparatus 100 may include any sensor, for example, an electrocardiogram (ECG) sensor, configured to sense a change in a biosignal or an exercise amount of the user based on the gait motion as well as the sensor portion 120 and the IMU sensor 130.

The controller 140 may control the driving portion 110 to output an assisting power, for example, an assisting torque, for assisting the gait of the user. As an example, when the walking assistance apparatus corresponds to the hip-type walking assistance apparatus, the driving portion 110 may include two driving portions. The controller 140 may output a control signal to the driving portion 110 such that the driving portion 110 outputs an assisting torque corresponding to the driving portion 110. The driving portion 110 may output the assisting torque based on the control signal output from the controller 140. In this example, the assisting torque may be set by an external source or by the controller 140.

Figure 2:
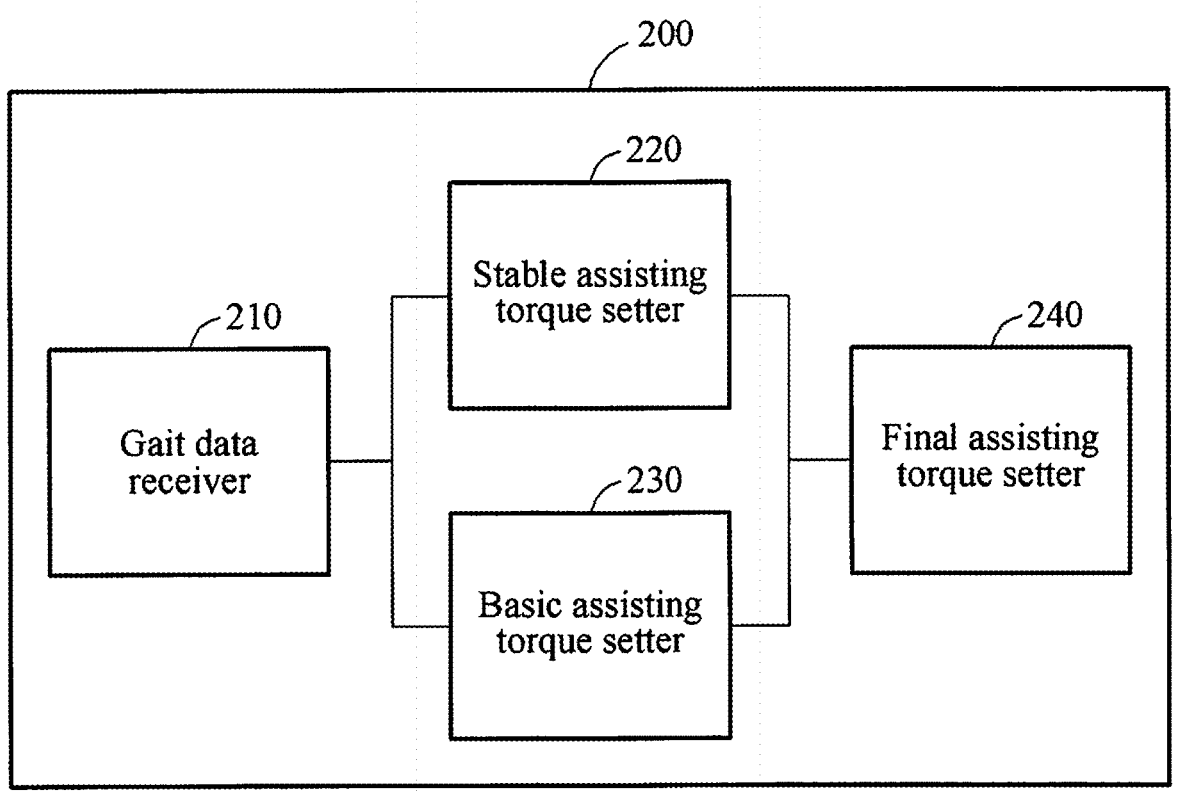
FIG. 2 illustrates an example of an assisting torque setting apparatus according to example embodiments.

FIG. 2 illustrates an assisting torque setting apparatus according to example embodiments.

Referring to FIG. 2, in some example embodiments an assisting torque setting apparatus 200 may be a separate apparatus physically independent of the walking assistance apparatus 100. In other example embodiments, the assisting torque setting apparatus 200 may be implemented as a logical model in the walking assistance apparatus 100.

A basic unit of a gait may be, for example, a step and a stride. The step may be classified based on a single heel strike. For example, the heel strike may indicate a state in which a sole of a foot is in contact with a ground. Also, the stride may be defined based on two steps.

The assisting torque setting apparatus 200 may include a gait data receiver 210, a stable assisting torque setter 220, a basic assisting torque setter 230, and a final assisting torque setter 240.

For example, in some example embodiments, as discussed below with reference to FIG. 17, the controller 140 may include a processor that when executing instructions stored in a memory, configures the processor to perform the functions of the gait data receiver 210, the stable assisting torque setter 220, the basic assisting torque setter 230, and the final assisting torque setter 240.

The gait data receiver 210 may receive, from a user, gait data obtained by sensing a change in an exercise amount of the user based on a gait motion. The gait data receiver 210 may receive the gait data from an external apparatus or a sensor for measuring the gait motion of the user, for example, the sensor portion 120. As an example, the gait data receiver 210 may receive information associated with both hip-joints of the user, for example, R-axial and L-axial joint angles and R-axial and L-axial joint angular velocities, from a potentiometer. As another example, the gait data receiver 210 may receive information associated with a moving direction of the both hip-joints, for example, X-axial, Y-axial, and Z-axial accelerations and X-axial, Y-axial, and Z-axial angular velocities, from an IMU sensor. In an example, the gait data receiver 210 may receive the gait data from any sensor capable of sensing the change in the exercise amount of the user based on the gait motion as well as the IMU sensor, the potentiometer, and the EMG sensor. For example, the gait data receiver 210 may receive, from the EMG sensor, EMG data indicating a change in an EMG of the user while the user is walking. Also, during the gait of the user, the gait data receiver 210 may receive pressure data and force from a pressure sensor and a force sensor, respectively.

Additionally, the gait data receiver 210 may receive the gait data of the user through a communication interface from an external apparatus including a sensor for measuring a gait motion of the user. The communication interface may include, for example, a wireless Internet interface such as a wireless local area network (WLAN), a wireless fidelity (WiFi) Direct, a digital living network alliance (DLNA), a wireless broadband (WiBro), a world interoperability for microwave access (WiMAX), a high speed downlink packet access (HSDPA), and the like, and a local area communication interface such as a Bluetooth™, a radio frequency identification (RFID), an infrared data association (IrDA), an ultra wideband (UWB), ZigBee, a near field communication (NFC), and the like. Also, the communication interface may indicate any interface, for example, a wired interface, to communicate with the external apparatus.

The stable assisting torque setter 220 may set a stable assisting torque using an evaluation value of at least one index based on the gait data. The stable assisting torque setter 220 may include an index evaluator, a weight calculator, and a stable assisting torque calculator.

The index evaluator may calculate an evaluation value of at least one index indicating a gait stability of the user based on the gait data of the user. In this example, the at least one index may include at least one of a gait symmetry, a stride length of the user, a stride width, a foot clearance, a landing speed, and a walk ratio.

In an example, the index evaluator may classify the gait data based on the stride, and calculate the evaluation value of the at least one index based on a result of the classifying. As an example, the index evaluator may classify the gait data based on the stride, by using the Z-axial acceleration acquired from the IMU sensor. As another example, the index evaluator may receive a sensing value corresponding to a time at which a foot of the user is in contact with the ground, from the pressure sensor or the force sensor disposed under the foot of the user, and classify the gait data based on the stride using the received sensing value. However, the present disclosure is not limited thereto. The index evaluator may use gait data classified based on the step, and gait data classified based on another unit as a reference.

The gait symmetry may indicate a degree of symmetry between both legs of the user. Each of the legs may swing or stand while the user is walking. When a balance of loads applied to muscles of the user is lost, one of the legs may be weakened and thus, a balance between a left leg and a right leg may not be maintained. To maintain the balance between the both legs, the index evaluator may incorporate the gait symmetry into an index.

The stride length, for example, a pace, may indicate a vertical length of a single stride in the gait motion of the user. The stride length may indicate, for example, a length between both legs in a state in which one of the legs swings and stands while another leg stands to be used a reference. When a muscular strength of the user decreases, the stride length may also decrease. Accordingly, the user may insufficiently use a dynamic energy in a body of the user during the gait thereby inducing a strain on the muscles. Through this, a reduction in the muscular strength may be aggravated. To avoid the foregoing, the index evaluator may incorporate the stride length into the index.

The stride width may indicate a horizontal length of the single stride in the gait motion of the user. When the muscular strength decreases, the user may increase a width between the both legs to maintain a balance therebetween. In this example, a relatively large amount of load may be applied to aduction and abduction muscles of a hip-joint such that a horizontal balance of the body is maintained. When the aduction and abduction muscles are incapable of accepting the load, the user may fall. To avoid this, the index evaluator may incorporate the stride width into the index.

The foot clearance may indicate a space between the foot of the user and the ground. In this example, the space may be, for example, a maximum length between the foot and the ground in a single stride, and a maximum length between a tip of the foot and the ground. In a normal state, the user may sufficiently bend an ankle of a leg swinging during the gait. When the muscular strength of the ankle decreases, the user may insufficiently bend the ankle during the gait and thus, the foot of the swinging leg may slump. Accordingly, the user may stub a toe of the foot against an obstacle on the ground, and then fall. To avoid this, the index evaluator may incorporate the foot clearance into the index.

The landing speed may indicate a speed of the foot arriving at the ground. In a normal state, the user may reduce a speed of a swinging leg at a landing point in time such that a contact force of the leg with the ground increases and the leg absorbs an impact with the ground. When the muscular strength decreases, the user may insufficiently reduce the speed and thus, may fall. To avoid this, the index evaluator may incorporate the landing speed into the index.

Also, the walk ratio may be defined as a ratio of the stride length to a cadence. In this example, the cadence may indicate a number of strides per predetermined reference time. The walk ratio may be used as a reference indicating efficiency of the gait of the user.

The index evaluator may set a threshold to determine whether the gait of the user is stable based on each index in advance. The index evaluator may compare the evaluation value and the threshold for each index, and determine whether the gait of the user is stable based on each index.

In an example, the index evaluator may estimate a similarity between a trajectory of a left hip-joint angle and a trajectory of a right hip-joint angle of the user in the gait data, and determine the estimated similarity as an evaluation value of the gait symmetry. In this example, the trajectory of the left hip-joint angle may differ from the trajectory of the right hip-joint angle by a single step.

The index evaluator may determine the evaluation value of the gait symmetry using Equation 1.

$$I_{sym}(n)=DTW(\theta_l(n),\theta_r(n)) \leq T_{sym} \quad [\text{Equation 1}]$$

In Equation 1, $I_{sym}(n)$ denotes an evaluation value of a gait symmetry in an $n^{th}$ stride, DTW denotes a dynamic time warping (DTW) scheme, denotes a trajectory of a left hip-joint angle in the $n^{th}$ stride, denotes a trajectory of a right hip-joint angle in the $n^{th}$ stride, and $T_{sym}$ denotes a threshold corresponding to the gait symmetry.

Since a left leg and a right leg swing alternately, a difference between times during which $\theta_l(n)$ and $\theta_r(n)$ are measured may correspond to a time required for one step.

The index evaluator may estimate a similarity between the trajectory of the left hip-joint angle in an $n^{th}$ left stride and the trajectory of the right hip-joint angle in an $n^{th}$ right stride based on the DTW scheme. The index evaluator may determine the estimated similarity as the evaluation value of the gait symmetry in the $n^{th}$ stride. When the evaluation value $I_{sym}(n)$ is less than or equal to the threshold $T_{sym}$, the index evaluator may determine that the gait of the user is stable based on the gait symmetry in the $n^{th}$ stride. Also, when the evaluation value $I_{sym}(n)$ is greater than the threshold $T_{sym}$, the index evaluator may determine that the gait of the user is unstable based on the gait symmetry in the nth stride.

In an example, the index evaluator may estimate an average stride length based on a left hip-joint angle range and a right hip-joint angle range, and determine the average stride length as the evaluation value of the stride length. In this example, to increase accuracy, the index evaluator may calculate an average of the left hip-joint angle range and an average of the right hip-joint angle range during a plurality of strides, and estimate a result of the calculating as the average stride length. In another example, the index evaluator may receive a sensing value from a pressure sensor or a force sensor disposed under the foot of the user, and estimate the average stride length based on the received sensing value. In this example, the sensing value may be obtained by the pressure sensor or the force sensor when the foot comes into contact with the ground.

The index evaluator may determine the evaluation value of the stride length based on Equation 2.

$$I_{str\_l(r)}(m) = \text{Average}(R_{l(r)}(n)) \geq T_{str\_l(r)} \quad \text{[Equation 2]}$$

In Equation 2, $I_{str\_l(r)}(m)$ denotes an $m^{th}$ evaluation value of the stride length of a left (or right) leg, $R_{l(r)}(n)$ denotes a left (or right) hip-joint angle range of n strides, and $T_{str\_l(r)}$ denotes a threshold corresponding to the stride length of the left (or right) leg.

For example, when n is 100, the index evaluator may calculate an average of the left hip-joint angle range and the right hip-joint angle range in 100 strides. In this example, the index evaluator may estimate a range from a minimum value to a maximum value of the left hip-joint angle as the left hip-joint angle range, and estimate a range from a minimum value to a maximum value of the right hip-joint angle as the right hip-joint angle range.

When the evaluation value $I_{str\_l(r)}(m)$ is greater than or equal to the threshold $T_{str\_l(r)}$, the index evaluator may determine that the gait of the user is unstable based on the stride length. Also, when the evaluation value $I_{str\_l(r)}(m)$ is less than the threshold $T_{str\_l(r)}$, the index evaluator may determine that the gait of the user is unstable based on the stride length.

In an example, the index evaluator may extract a maximum flexion angle of the left hip-joint and a maximum flexion angle of the right hip-joint from the gait data, and determine the maximum flexion angle of the left hip-joint and the maximum flexion angle of the right hip-joint as the evaluation value of the foot clearance. In a normal state, the user may lift a foot tip of a swinging leg using an ankle muscle during the gait. When a muscular strength of the ankle decreases, the user may lift an entire swinging leg using a hip-joint muscle and thus, the foot-tip may be lifted to a lower height as compared to the normal state. Since the maximum flexion angle of the left hip-joint and the maximum flexion angle of the right hip-joint indicate whether the ankle muscle is in the normal state, the index evaluator may determine the maximum flexion angle of the left hip-joint and the maximum flexion angle of the right hip-joint as the evaluation value of the foot clearance.

The index evaluator may determine the evaluation value of the foot clearance based on Equation 3.

$$I_{clr\_l(r)}(m) = \max(M_{l(r)}(n)) \geq T_{clr\_l(r)} \quad \text{[Equation 3]}$$

In Equation 3, $I_{clr\_l(r)}(m)$ denotes an $m^{th}$ evaluation value of the foot clearance of the left (right) leg, $M_{l(r)}(n)$ denotes flexion angles of the left (right) leg in n strides, $\max(M_{l(r)}(n))$ denotes a maximum flexion angle of the flexion angles of the left (right) leg, and $T_{clr\_l(r)}$ denotes a threshold corresponding to the foot clearance of the left (right) leg.

For example, when n is 100, the index evaluator may extract the maximum flexion angle of the left hip-joint and the maximum flexion angle of the right hip-joint in 100 strides.

When the evaluation value $I_{clr\_l(r)}(m)$ is greater than or equal to the threshold $T_{clr\_l(r)}$, the index evaluator may determine that the gait of the user is stable based on the foot clearance. Also, when the evaluation value $I_{clr\_l(r)}(m)$ is less than the threshold $T_{clr\_l(r)}$, the index evaluator may determine that the gait of the user is unstable based on the foot clearance.

The weight calculator may calculate a weight of at least one index based on a difference between an evaluation value of the at least one index and a threshold corresponding to the at least one index. The weight calculator may calculate the weight of the at least one index by normalizing the difference between the evaluation value of the at least one index and the threshold corresponding to the at least one index, as shown in Equation 4 below.

$$w_{i\_l(r)}(k) = \frac{|I_{i\_l(r)}(k) - T_{i\_l(r)}(k)|}{V_{i\_l(r)}} \quad \text{[Equation 4]}$$

In Equation 4, $W_{i\_l(r)}(k)$ denotes a $k^{th}$ weight of an index i of the left (right) leg, $I_{i\_l(r)}(k)$ denotes a $k^{th}$ evaluation value of the index i of the left (right) leg, $T_{i\_l(r)}(k)$ denotes a $k^{th}$ threshold of the index i of the left (right) leg, and $V_{i\_l(r)}$ denotes a normalizing value of the index i of the left (right) leg. Based on Equation 4, the weight may increase according to an increase in a difference between an evaluation value and a threshold of an index. In an example, the weight calculator may set "0" as a weight of an index for which the index evaluator determines that the gait of the user is stable.

The stable assisting torque calculator may calculate a stable assisting torque by applying the weight to an initial stable assisting torque corresponding to the at least one index. The stable assisting torque may indicate, for example, a force provided from the walking assistance apparatus such that the user stably performs the gait. The initial stable assisting torque may indicate an initial value of the stable assisting torque, and correspond to each of the at least one index. The initial stable assisting torque may be set in advance, or set by the stable assisting torque calculator based on the gait data.

In an example, the stable assisting torque calculator may set an initial stable assisting torque for the gait symmetry based on the difference between the trajectory of the left hip-joint angle and the trajectory of the right hip-joint angle in the gait data. The stable assisting torque calculator may set the initial stable assisting torque for the gait symmetry based on Equations 5 through 7.

A difference between a time at which a left leg stride starts and a time at which a right leg stride starts may correspond to a time required for one step. A difference between the left hip-joint angle and the right hip-joint angle may be calculated based on the difference in time.

In an example a variable p may be used to apply the difference in time. The variable p may be a variable obtained by normalizing a stride trajectory. For example, the variable p may indicate a location of an entire stride trajectory in which a start of stride is 0 and an end of stride is 1.

A time obtained by normalizing a time at which a stride is performed based on the variable p may be defined as, for example, a normalized stride time (NST).

In the same NST, the difference between the left hip joint angle and the right hip joint angle may be calculated based on Equation 5 as shown below.

$$\Delta\theta(p) = \theta_r(p) - \theta_l(p) \quad \text{[Equation 5]}$$

In Equation 5, $\theta_r(p), \theta_l(p)$ denotes the left hip joint angle and the right hip joint angle measured at a p NST, respectively.

An assistance torque for ameliorating an asymmetry may be calculated based on Equations 6 and 7 as shown below.

$$p_{r(l)} = \frac{t - t_{s\_r(l)}}{t_d} \qquad \text{[Equation 6]}$$

In Equation 6, $t_{s\_r(l)}$ denotes a time at which the right leg (left leg) stride starts, and $t_d$ denotes a time during which one stride is performed. $P_{r(l)}$ denotes an NST in a right leg (left leg) stride trajectory with respect to a point in time t after $t_{s\_r(l)}$.

$$\tau_{pri\_sym\_l}(t) = K_{sym\_l} \Delta\theta(p_l)$$

$$\tau_{pri\_sym\_r}(t) = -K_{sym\_r} \Delta\theta(p_r)$$

$K_{sym\_l(r)}$: Gain for Symmetry Assist  [Equation 7]

In Equation 7, $\tau_{pri\_sym\_l}(t)$ denotes an initial stable assisting torque of the gait symmetry provided to the left leg based on the point in time t, $\tau_{pri\_sym\_r}(t)$ denotes an initial stable assisting torque of the gait symmetry provided to the right leg based on the point in time t, $K_{sym\_l}$ denotes a gain of the initial stable assisting torque of the gait symmetry provided to the left leg, and $K_{sym\_r}$ denotes a gain of the initial stable assisting torque of the gait symmetry provided to the right leg. Based on Equation 7, an assistance torque after $t_{s\_r(l)}$ may be determined.

In an example, when the one stride terminates, a point in time at which a subsequent stride starts and $\Delta\theta(p)$ may be updated and a stable assistance torque for a gait symmetry may be calculated repetitively.

Also, the gain $K_{sym\_l}$ and the gain $K_{sym\_r}$ may be set in advance. Based on Equation 7, when the difference between the trajectory of the left hip-joint angle and the trajectory of the right hip-joint angle is generated, the stable assisting torque calculator may set the initial stable assisting torque to offset the difference.

In an example, the stable assisting torque calculator may extract an intersecting point in time between the left leg and the right leg of the user, and set a peak torque for a desired (or, alternatively, a predetermined) period of time from the intersecting point in time as the initial stable assisting torque for the stride length. In this example, the desired (or, alternatively, predetermined) period of time and the peak torque may be set in advance. The stable assisting torque calculator may set the initial stable assisting torque for the stride length based on Equation 8 as shown below.

$$\tau_{pri\_sym\_l}(t) = f_{str\_l}(\theta_r(t), \theta_l(t), I_{str\_l}(n), \tau_{str\_peak\_l}, t_{dur\_l})$$

$$\tau_{pri\_sym\_r}(t) = f_{str\_r}(\theta_r(t), \theta_l(t), I_{str\_r}(n), \tau_{str\_peak\_r}, t_{dur\_r}) \qquad \text{[Equation 8]}$$

In Equation 8, $\tau_{pri\_str\_l}(t)$ denotes an initial stable assisting torque of the stride length provided to the left leg based on the point in time t, $\tau_{pri\_str\_r}(t)$ denotes an initial stable assisting torque of the stride) length provided to the right leg based on the point in time t, $\theta_l(t)$ denotes the trajectory of the left hip joint angle corresponding to the point in time t, and $\theta_r(t)$ denotes the trajectory of the right hip joint angle corresponding to the point in time t, $I_{str\_l}(n)$ denotes the evaluation value of the stride length of the left leg, and $I_{str\_r}(n)$ denotes the evaluation value of the stride length of the right leg. Also, $\tau_{str\_peak\_l}$ denotes a peak torque of the stride length provided to the left leg, $\tau_{str\_peak\_r}$ denotes a peak torque of the stride length provided to the right leg, $t_{dur\_l}$ denotes a desired (or, alternatively, predetermined) period of time during which the initial stable assisting torque of the stride length is provided to the left leg, and $t_{dur\_r}$ denotes a desired (or, alternatively, predetermined) period of time during which the initial stable assisting torque of the stride length is provided to the right leg.

Based on Equation 8, the stable assisting torque calculator may extract the intersecting point in time using the trajectory $\theta_l(t)$ of the left hip-joint angle corresponding to the point in time t and the trajectory $\theta_r(t)$ of the right hip-joint angle corresponding to the point in time t, and provide the peak torque $\tau_{str\_peak\_l}$ and the peak torque $\tau_{str\_peak\_r}$ such that the left leg and the right leg are spaced apart from one another during the period of time $t_{dur\_l}$ and $t_{dur\_r}$ from the intersecting point in time.

In an example, the stable assisting torque calculator may extract a point in time at which the swinging leg of the user approaches the ground, and set the initial stable assisting torque of the foot clearance using a peak torque of a desired (or, alternatively, predetermined) period of time from the extracted point in time. In this example, the desired (or, alternatively, predetermined) period of time and the peak torque may be set in advance. The stable assisting torque calculator may set the initial stable assisting torque of the foot clearance based on Equation 9 as shown below.

$$\tau_{pri\_clr\_l}(t) = f_{clr\_l}(\theta_r(t), \theta_l(t), I_{clr\_l}(n), \tau_{clr\_peak\_l}, t_{dur\_l})$$

$$\tau_{pri\_clr\_r}(t) = f_{clr\_r}(\theta_r(t), \theta_l(t), I_{clr\_r}(n), \tau_{clr\_peak\_r}, t_{dur\_r}) \qquad \text{[Equation 9]}$$

In Equation 9, $\tau_{pri\_clr\_l}(t)$ denotes an initial stable assisting torque of the foot clearance provided to the left leg based on the point in time t, $\tau_{pri\_clr\_r}(t)$ denotes an initial stable assisting torque of the foot clearance provided to the right leg based) on the point in time t, $\theta_l(t)$ denotes the trajectory of the left hip-joint angle corresponding to the point in time t, and $\theta_r(t)$ denotes the trajectory of the right hip-joint angle corresponding to the point in time t, $I_{clr\_l}(n)$ denotes the evaluation value of the foot clearance of the left leg, and $I_{clr\_r}(n)$ denotes the evaluation value of the foot clearance of the right leg. Also, $\tau_{clr\_peak\_l}$ denotes a peak torque of the foot clearance provided to the left leg, $\tau_{clr\_peak\_r}$ denotes a peak torque of the foot clearance provided to the right leg, $t_{dur\_l}$ denotes a desired (or, alternatively, period) of time during which the initial stable assisting torque of the foot clearance is provided to the left leg, and $t_{dur\_r}$ denotes a desired (or, alternatively, predetermined) period of time during which the initial stable assisting torque of the foot clearance is provided to the right leg. Based on Equation 9, the stable assisting torque calculator may extract the point in time at which the swinging leg of the user approaches the ground using the trajectory $\theta_l(t)$ of the left hip-joint angle and the trajectory $\theta_r(t)$ of the right hip-joint angle corresponding to the point in time t, and provide the peak torque $\tau_{clr\_peak\_l}$ and the peak torque $\tau_{clr\_peak\_r}$ such that the left leg and the right leg are lifted to an increased height during the period of time $t_{dur\_l}$ and $t_{dur\_r}$ from the extracted point in time.

The stable assisting torque calculator may set the assisting torque by applying the weight to the initial stable assisting torque for each of the at least one index. In an example, the stable assisting torque calculator may determine the assisting torque based on Equation 10 as shown below.

$$\tau_{stab\_l(r)}(n) = \sum_i w_{i\_l(r)}(n) \cdot \tau_{pri\_i\_l(r)}(n) \qquad \text{[Equation 10]}$$

In Equation 10, $\tau_{stab\_l(r)}(n)$ denotes an assisting torque provided to the left (right) leg in the $n^{th}$ stride, $W_{i\_l(r)}(k)$ denotes a $k^{th}$ weight of an index i of the left (right) leg, and $\tau_{pri\_i\_l(r)}(n)$ denotes an initial stable assisting torque of the index i provided to the left (right) leg.

In an example, the stable assisting torque calculator may set the assisting torque at an interval of a single stride. In this example, an interval of calculating the evaluation value and the weight may differ for each index. For example, the stable assisting torque calculator may calculate the evaluation value and the weight of the gait symmetry at an interval of the single stride, and calculate the evaluation values and the weights of the stride length and the foot clearance at an interval of 100 strides. In this example, the stable assisting torque calculator may calculate the evaluation value and the weight of the gait symmetry for each single stride and use a result of the calculating to set the assisting torque at an interval of the single stride. Also, the stable assisting torque calculator may set the assisting torque at an interval of the single stride based on the evaluation values and the weights of the stride length and the foot clearance, which are calculated in advance.

The basic assisting torque setter 230 may set a basic assisting torque corresponding to a gait motion of the user based on the gait data. The basic assisting torque may be, for example, an assisting torque basically set by the assisting torque setting apparatus 200 to assist the gait of the user irrespective of the evaluation value of the at least one index. The basic assisting torque setter 230 may set the basic assisting torque based on an adaptive oscillator (AO)-based basic assisting torque setting scheme or a finite state machine (FSM)-based basic assisting torque setting scheme. In this example, whether the basic assisting torque setter 230 applies the AO-based basic assisting torque setting scheme or the FSM-based basic assisting torque setting scheme may be determined by an external source through a communication interface or by the basic assisting torque setter 230 through an analysis on a muscular strength or a gait pattern of the user.

In the AO-based basic assisting torque setting scheme, the basic assisting torque setter 230 may apply the gait data to an AO and estimate a periodicity, for example, a frequency pattern and a phase pattern, of the gait motion of the user, thereby setting an assisting torque corresponding to the periodicity as the basic assisting torque. In this example, an assisting torque corresponding to each periodicity may be set in advance. As an example, a basic assisting torque set based on the AO-based basic assisting torque setting scheme may be appropriately used by a user performing a gait at a gait speed of a normal pedestrian or a user performing a gait regularly.

In the FSM-based basic assisting torque setting scheme, the basic assisting torque setter 230 may model a plurality of gait states in advance, and recognize a gait state corresponding to the gait motion of the user from among the modeled gait states. Also, the basic assisting torque setter 230 may set an assisting torque provided based on the recognized gait state as the basic assisting torque. In this example, an assisting torque corresponding to each of the gait states may be set in advance. As an example, a basic assisting torque set based on the FSM-based basic assisting torque setting scheme may be appropriately used by a user unable to perform a gait at a gait speed of a typical pedestrian or a user performing a gait irregularly.

For example, the basic assisting torque setter 230 may utilize the FSM to assist a user in smoothly walking. As the user moves through various gait states in a walking cycle, the basic assisting torque setter 230 may vary an amount of torque provided to the user. For example, the basic assisting torque setter 230 may instruct the walking assistance apparatus 100 to increase the torque, when the user is increasing a pace of walking on a flat surface, a sloped surface or a stepped surface. Likewise, the basic assisting torque setter 230 may instruct the walking assistance robot to increase a damping torque applied to a leg of the user, when the user is decreasing a pace of walking on the flat surface, the sloped surface or the stepped surface.

In some example embodiments, the controller 140 is configured to calculate an intended motion of the user, and calculate the basic assistance torque to apply to joints thereof based on the intended motion.

Since the natural walking motion may include moving the "right arm and left leg" in one direction while moving the "left arm and right leg" in the other direction, in some example embodiments, the sensor portion 120 may include one or more sensors that detect when one or more of a left and right arms are moving forward or background after passing the climax in front of or behind the user's body, and may generate signals that allow the controller 140 to determine a moving direction of the user's arms. For example, if the sequence of detected signals include detection by a first sensor located anterior of the user and then by a second sensor located posterior of the user, the controller 140 may determine that the user's associated arm is moving backward and accordingly estimate that the user's other arm is moving forward. In contrast, if the sequence of detected signals include detection by the second sensor and then by the first sensor, the controller 140 may determine that the user's associated arm is moving forward and accordingly estimate that the user's other arm is moving forward.

The controller 140 may control the basic assisting torque provided to each of the legs of the user such that, if the controller 140 determines that the user's left arm is moving forward and the right arm is moving backward, the basic assisting torque is provided to move the user's right leg forward while supporting the left leg. Likewise, if the controller 140 determines that the user's left arm is moving backward and the right arm is moving forward, the basic assisting torque may be provided to move the user's left leg forward while supporting the right leg.

In other example embodiments, the controller 140 is configured to determine an amount of the basic assistance torque based on terrain information, including an unevenness or a shape of the terrain. For example, the sensor portion 120 may include an image capturing unit, such as a camera that collects image data regarding the terrain by transforming visible rays or infrared rays transmitted thereto. Further, the sensor portion 120 may include a 3D depth sensor that, for example, radiates infrared rays onto the terrain, may receive the infrared rays reflected from the terrain and then may detect a shape or position of the terrain based on the received infrared rays.

The sensor portion 110 may transmit the image data to the controller 140. The controller 140 may generate the ground information such that the terrain information represents a map of the terrain. Further the controller 140 may classify the terrain information based on data contained therein. For example, the controller 140 may classify the terrain as being uphill stairs, downhill stairs, uphill inclination, downhill inclination, or a flat terrain. The controller 140 may adjust the amount of basic assistance torque provided to the user based on the classification of the terrain. The assisting torque setting apparatus 200 may further include a gait motion recognizer configured to recognize the gait motion of the user based on the gait data.

The gait motion recognizer may determine whether the user performs the gait motion based on the gait data. When the gait motion recognizer determines that the user performs the gait motion, the basic assisting torque setter 230 may set the basic assisting torque based on the gait data. When the gait motion recognizer determines that the user does not perform the gait motion, the basic assisting torque setter 230 may set the basic assisting torque to be "0".

The final assisting torque setter 240 may set a final assisting torque based on the basic assisting torque and the stable assisting torque. In an example, the final assisting torque setter 240 may set the final assisting torque by adding the stable assisting torque to the basic assisting torque. Also, the final assisting torque setter 240 may set, as the final assisting torque, a greater of the absolute value of the basic assisting torque and the absolute value of the stable assisting torque. In another example, the final assisting torque setter 240 may set the stable assisting torque as the final assisting torque. However, the present disclosure is not limited thereto. The final assisting torque setter 240 may also set the final assisting torque by combining the basic assisting torque and the stable assisting torque based on various methods.

In an example, the final assisting torque setter 240 may use the communication interface to transmit information associated with the stable assisting torque, information associated with the basic assisting torque, and information associated with the final assisting torque to an external apparatus, for example, a server and the walking assistance apparatus 100.

Also, the final assisting torque setter 240 may control the walking assistance apparatus 100 to output the stable assisting torque or the final assisting torque. Accordingly, the walking assistance apparatus 100 controlled by the final assisting torque setter 240 may assist the user to stably perform the gait based on the stable assisting torque or the final assisting torque, thereby protect the user from an accidental fall.

Figure 3:
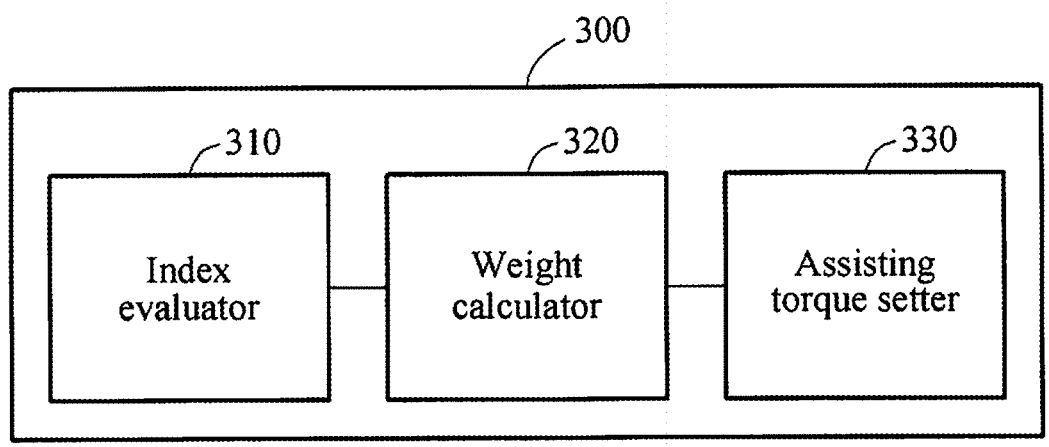
FIG. 3 illustrates another example of an assisting torque setting apparatus according to example embodiments.

FIG. 3 illustrates an assisting torque setting apparatus according to example embodiments.

Referring to FIG. 3, the assisting torque setting apparatus 300 includes an index evaluator 310, a weight calculator 320, and an assisting torque setter 330.

The index evaluator 310 may calculate an evaluation value of at least one index indicating a gait stability of a user based on gait data of the user. In this example, the at least one index may include at least one of a gait symmetry, a stride length, a stride width, a foot clearance, a landing speed, and a walk ratio.

The index evaluator 310 may classify the gait data based on a stride, and calculate the evaluation value of the at least one index based on the classified gait data. In this example, the index evaluator 310 may calculate an evaluation value of the gait symmetry based on Equation 1, calculate an evaluation value of the stride length based on Equation 2, and calculate an evaluation value of the foot clearance based on Equation 3. Also, the index evaluator 310 may compare an evaluation value and a threshold for each index, and determine whether the gait of the user is stable based on a corresponding index as a reference.

The weight calculator 320 may calculate a weight of the at least one index based on a difference between the evaluation value of the at least one index and a threshold corresponding to the at least one index. In this example, as shown in Equation 4, the weight calculator 320 may calculate the weight of the at least one index by normalizing the difference between the evaluation value of the at least one index and the threshold corresponding to the at least one index.

The assisting torque setter 330 may set a stable assisting torque by applying the weight to an initial stable assisting torque corresponding to the at least one index.

The assisting torque setter 330 may set the initial stable assisting torque based on the gait data, and set the stable assisting torque by applying the weight to the initial stable assisting torque. As an example, the assisting torque setter 330 may set an initial stable assisting torque of the gait symmetry based on Equation 7, set an initial stable assisting torque of the stride length based on Equation 8, and set an initial stable assisting torque of the foot clearance based on Equation 9.

Also, the assisting torque setter 330 may set the stable assisting torque by applying the weight to the initial stable assisting torque for each of the at least one index. As an example, the assisting torque setter 330 may determine the stable assisting torque based on Equation 10.

Additionally, the assisting torque setting apparatus 300 may include a basic assisting torque setter configured to set a basic assisting torque corresponding to the gait motion of the user based on the gait data.

The basic assisting torque setter may set the basic assisting torque corresponding to the gait motion of the user based on the gait data. The basic assisting torque setter may set the basic assisting torque based on, for example, an AO-based basic assisting torque setting scheme and an FSM-based basic assisting torque setting scheme. In an example, whether the basic assisting torque setter applies the AO-based basic assisting torque setting scheme or the FSM-based basic assisting torque setting scheme may be determined by an external source through a communication interface or by the basic assisting torque setter through an analysis on a muscular strength or a gait pattern of the user.

In the AO-based basic assisting torque setting scheme, the basic assisting torque setter may estimate a periodicity of the gait motion of the user by applying the gait data to an AO, and set an assisting torque corresponding to the periodicity as the basic assisting torque.

In the FSM-based basic assisting torque setting scheme, the basic assisting torque setter may model a plurality of gait states in advance, and recognize a gait state corresponding to the gait motion of the user from among the modeled gait states. Also, the basic assisting torque setter may set an assisting torque provided based on the recognized gait state as the basic assisting torque.

The assisting torque setter 330 may set a final assisting torque based on the basic assisting torque and the stable assisting torque. In an example, the assisting torque setter 330 may set the final assisting torque by combining the stable assisting torque and the basic assisting torque. Also, the assisting torque setter 330 may set a value having a greater absolute value between the basic assisting torque and the stable assisting torque as the final assisting torque. In another example, the assisting torque setter 330 may set the stable assisting torque as the final assisting torque. However, the present disclosure is not limited thereto. The final assisting torque setter 240 may also set the final assisting torque by combining the basic assisting torque and the stable assisting torque based on various methods.

Figure 4:
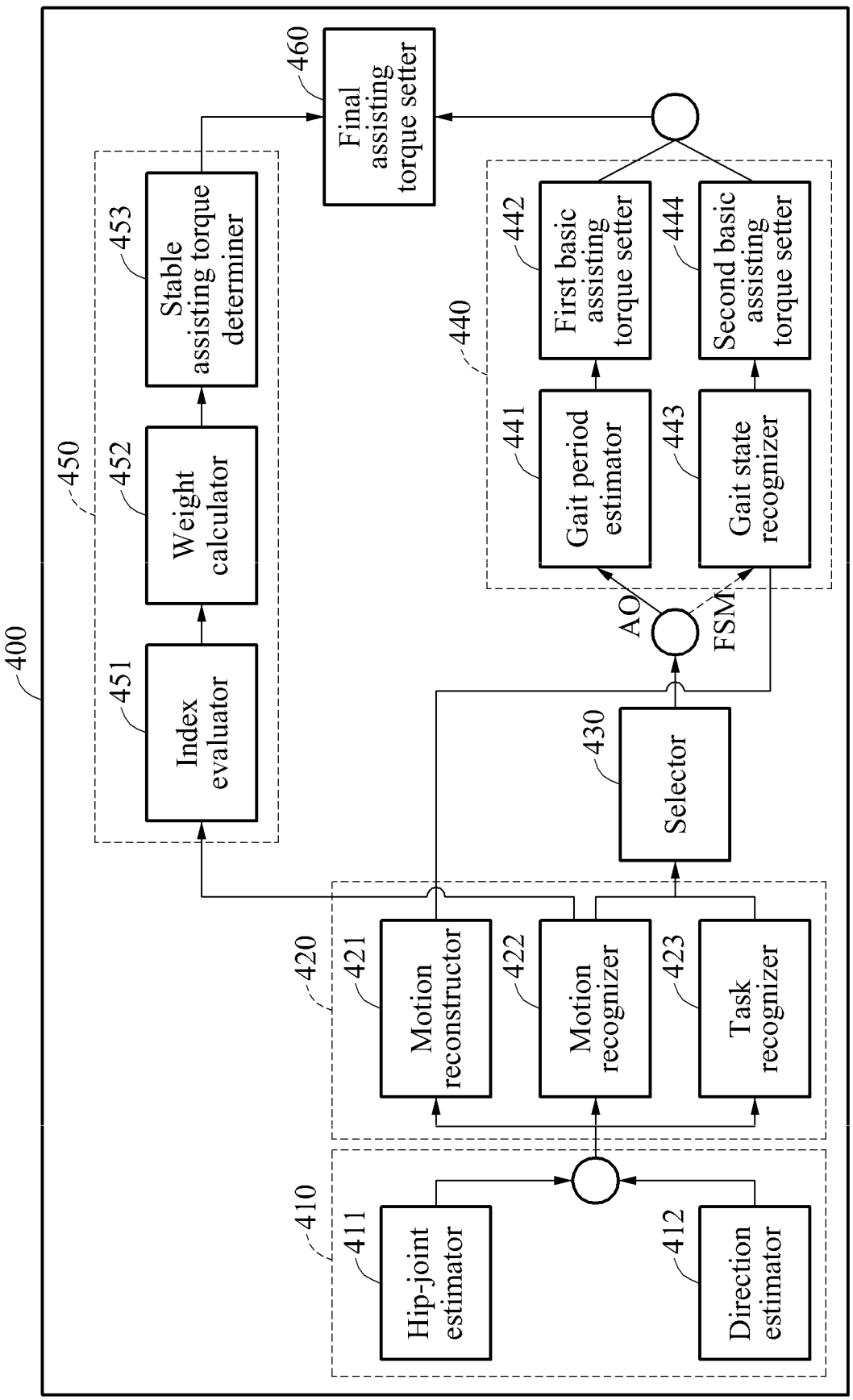
FIG. 4 illustrates still another example of an assisting torque setting apparatus according to example embodiments.

FIG. 4 illustrates an assisting torque setting apparatus according to example embodiments.

Referring to FIG. 4, an assisting torque setting apparatus 400 includes a gait data extractor 410, a motion estimator 420, a selector 430, a basic assisting torque setting unit 440, a stable assisting torque setter 450, and a final assisting torque setter 460.

The gait data extractor 410 includes a hip-joint estimator 411 and a direction estimator 412. The hip-joint estimator 411 may estimate information associated with both hip-joints angles, both hip-joints velocities, and both hip-joints angular velocities. As an example, the hip-joint estimator 411 may receive two-axial joint angle data and two-axial angular velocity data from a potentiometer. As another example, the hip-joint estimator 411 may receive information associated with the hip-joints angles, the both hip-joints velocities, and the both hip-joints angular velocities from a motor encoder. The hip-joint estimator 411 may estimate information associated with hip-joints based on the information received from the potentiometer or the motor encoder.

The direction estimator 412 may estimate information on a moving direction of the hip-joints. For example, the direction estimator 412 may receive, from an IMU sensor, X-axial, Y-axial, and Z-axial acceleration data and X-axial, Y-axial, and Z-axial angular velocity data based on the gait motion of the user. The direction estimator 412 may estimate the moving direction of the hip-joints based on the data received from the IMU sensor.

The motion estimator 420 includes a motion reconstructor 421, a motion recognizer 422, and a task recognizer 423.

The motion reconstructor 421 may estimate a posture of the user based on the gait data acquired by the gait data extractor 410. For example, the motion reconstructor 421 may estimate a posture of an angle or a knee based on the information associated with the hip-joints acquired by the hip-joint estimator 411.

The motion recognizer 422 may estimate a posture, for example, a standing posture, a sitting posture, and a walking posture, of the user based on the gait data acquired by the gait data extractor 410.

The task recognizer 423 may estimate a gait task, for example, a gait environment, of the user based on the gait data acquired by the gait data extractor 410. For example, the task recognizer 423 may recognize a level walking task, an ascending gait task, a descending gait task, a stepping-up gait task, and a stepping-down gait task. However, a type of the gait task is not limited thereto. The task recognizer 423 may recognize various gait tasks as well as the aforementioned gait tasks.

The selector 430 may select a scheme of setting the basic assisting torque. For example, the selector 430 may select an AO-based basic assisting torque setting scheme or an FSM-based basic assisting torque setting scheme. In this example, the selector 430 receive a basic assisting torque setting scheme selected by an external source through a communication interface, or may select the basic assisting torque setting scheme by analyzing a muscular strength or a gait pattern of the user.

The basic assisting torque setting unit 440 includes a gait period estimator 441, a first basic assisting torque setter 442, a gait state recognizer 443, and a second basic assisting torque setter 444.

When the selector 430 selects the AO-based basic assisting torque setting scheme, the gait period estimator 441 may estimate a periodicity of the gait motion of the user by applying the gait data to an AO. For example, the gait period estimator 441 may extract a periodical frequency pattern or phase pattern from the gait of the user by applying the gait data to the AO. The first basic assisting torque setter 442 may set an assisting torque corresponding to the periodicity of the gait motion as the basic assisting torque. As an example, the first basic assisting torque setter 442 may set a plurality of frequency patterns and an assisting torque corresponding to each of the plurality of a frequency patterns in advance. The first basic assisting torque setter 442 may extract a frequency pattern corresponding to the frequency pattern extracted by the gait period estimator 441, from among the plurality of frequency patterns. Subsequently, the first basic assisting torque setter 442 may extract the assisting torque corresponding to the frequency pattern extracted by the first basic assisting torque setter 442, from among assisting torques corresponding to the plurality of frequency patterns. Similarly, the first basic assisting torque setter 442 may perform the above operation on the phase patterns.

When the selector 430 selects the FSM-based basic assisting torque setting scheme, the gait period estimator 441 may recognize a gait state corresponding to the gait motion of the user from among a plurality of gait states modeled by applying the gait data to an FSM. For example, the gait state recognizer 443 may model the plurality of gait states in advance. As an example, the gait state recognizer 443 may classify the gait states into a state in which a right leg swings, a state in which both legs intersect one another, and a state in which a left leg swings, and then may model the classified gait states. The gait state recognizer 443 may recognize the gait state of the user by applying the gait data to the FSM. Also, the gait state recognizer 443 may recognize the gait state of the user based on the posture of the user estimated in the motion reconstructor 421. The gait state recognizer 443 may extract a gait state corresponding to the recognized gait state from among the modeled gait states.

The second basic assisting torque setter 444 may set an assisting torque corresponding to the gait state extracted from among the modeled gait states, as the basic assisting torque. In this example, an assisting torque corresponding to each of the gait states may be set in advance.

The stable assisting torque setter 450 includes an index evaluator 451, a weight calculator 452, and a stable assisting torque determiner 453.

The index evaluator 451 may classify the gait data based on a stride, and calculate an evaluation value of at least one index based on the classified gait data. In this example, the index evaluator 451 may calculate an evaluation value of a gait symmetry based on Equation 1, calculate an evaluation value of a stride length based on Equation 2, and calculate an evaluation value of a foot clearance based on Equation 3. Also, the index evaluator 451 may compare an evaluation value and a threshold for each index, and determine whether the gait of the user is stable based on a corresponding index as a reference.

In an example, when the motion recognizer 422 recognizes that the user does not perform the gait, the stable assisting torque may not be set and thus, the index evaluator 451 may not calculate the evaluation value of the at least one index.

The weight calculator 452 may calculate a weight of the at least one index based on a difference between the evaluation value of the at least one index and a threshold corresponding to the at least one index. In this example, as shown in Equation 4, the weight calculator 452 may calculate the weight of the at least one index by normalizing the difference between the evaluation value of the at least one index and the threshold corresponding to the at least one index. The stable assisting torque determiner 453 may set an initial stable assisting torque based on the gait data, and set the stable assisting torque by applying the weight to the initial stable assisting torque. As an example, the stable assisting torque determiner 453 may set an initial stable assisting torque of the gait symmetry based on Equation 7, set an initial stable assisting torque of the stride length based on Equation 8, and set an initial stable assisting torque of the foot clearance based on Equation 9.

The stable assisting torque determiner 453 may determine the stable assisting torque by applying the weight to the initial stable assisting torque, for each of the at least one index. As an example, the stable assisting torque determiner 453 may determine the stable assisting torque based on Equation 10.

The final assisting torque setter 460 may set a final assisting torque based on the basic assisting torque set in the basic assisting torque setting unit 440 and the stable assisting torque set in the stable assisting torque determiner 450. The final assisting torque setter 460 may set the final assisting torque by combining the stable assisting torque and the basic assisting torque. Additionally, the final assisting torque setter 460 may set a value having a greater absolute value between the basic assisting torque and the stable assisting torque as the final assisting torque. Also, the final assisting torque setter 460 may set the stable assisting torque as the final assisting torque.

Figure 5:
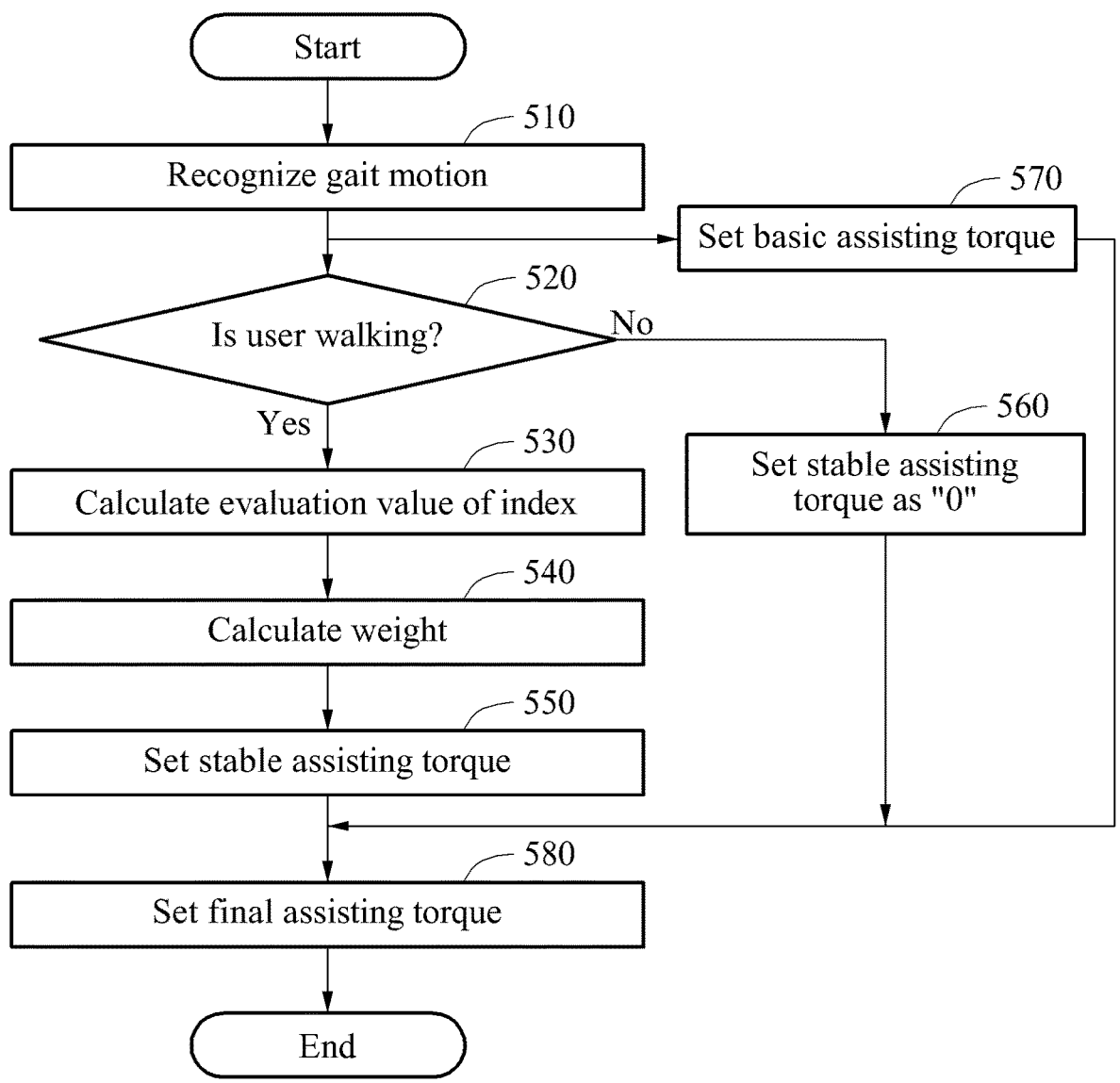
FIG. 5 illustrates an example of setting a final assisting torque according to example embodiments.

FIG. 5 illustrates an example of setting a final assisting torque according to example embodiments.

Referring to FIG. 5, in operation 510, an assisting torque setting apparatus recognizes a gait motion of a user. The assisting torque setting apparatus may acquire gait data from a sensor configured to sense a motion of the user, and estimate the motion based on the acquired gait data.

In operation 520, the assisting torque setting apparatus determines whether the user is walking. In operation 560, in response to a determination that the user is not walking, the assisting torque setting apparatus sets a stable assisting torque as "0".

As discussed in more detail below, in operations 530, 540 and 550, in response to determining that the user is walking, the stable assisting torque setter 220, 300, 450 calculates an evaluation value of an index (operation 530), calculates a weight of the index (operation 540), and sets the stable assisting torque (operation 550).

In operation 530, in response to a determination that the user is walking, the assisting torque setting apparatus (e.g., the index evaluator 310, 451) calculates an evaluation value of at least one index. As an example, the assisting torque setting apparatus may calculate an evaluation value of a gait symmetry based on Equation 1, calculate an evaluation value of a stride length based on Equation 2, and calculate an evaluation value of a foot clearance based on Equation 3.

In operation 540, the assisting torque setting apparatus (e.g., the weight calculator 320, 452) calculates a weight of the at least one index. The assisting torque setting apparatus may calculate the weight of the at least one index based on a difference between the evaluation value of the at least one index and a threshold corresponding to the at least one index. In this example, as shown in Equation 4, the assisting torque setting apparatus may calculate the weight of the at least one index by normalizing the difference between the evaluation value and the threshold.

In operation 550, the assisting torque setting apparatus (e.g., assistance torque setter 330 or the stable assisting torque determiner 453) sets the stable assisting torque. The assisting torque setting apparatus may set an initial stable assisting torque based on the gait data, and set the stable assisting torque by applying the weight to the initial stable assisting torque. As an example, the assisting torque setting apparatus may set an initial stable assisting torque of the gait symmetry based on Equation 7, set an initial stable assisting torque of the stride length based on Equation 8, and set an initial stable assisting torque of the foot clearance based on Equation 9. Also, the assisting torque setting apparatus may set the stable assisting torque by applying the weight to the initial stable assisting torque for each of the at least one index. As an example, the assisting torque setting apparatus may determine the stable assisting torque based on Equation 10.

In operation 570, the assisting torque setting apparatus (e.g., the basic assisting torque setter 230, 440) sets a basic assisting torque corresponding to the gait motion of the user based on the gait data. The assisting torque setting apparatus may set the basic assisting torque using an AO-based basic assisting torque setting scheme and an FSM-based basic assisting torque setting scheme. In the AO-based basic assisting torque setting scheme, the assisting torque setting apparatus may estimate a periodicity of the gait motion of the user by applying the gait data to an AO, and set an assisting torque corresponding to the periodicity as the basic assisting torque. In the FSM-based basic assisting torque setting scheme, the assisting torque setting apparatus may model a plurality of gait states in advance, and recognize a gait state corresponding to the gait motion of the user from among the modeled gait states by applying the gait data to an FSM. Also, the assisting torque setting apparatus may set an assisting torque corresponding to the recognized gait state as the basic assisting torque.

In operation 580, the assisting torque setting apparatus (e.g. the final assisting torque setter 240, 460) sets a final assisting torque by combining the stable assisting torque and the basic assisting torque. The assisting torque setting apparatus may set the final assisting torque by obtaining a sum of the stable assisting torque and the basic assisting torque. Additionally, the assisting torque setting apparatus may set a value having a greater absolute value between the stable assisting torque and the basic assisting torque, as the final assisting torque. Also, the assisting torque setting apparatus may set the stable assisting torque as the final assisting torque.

Figure 6:
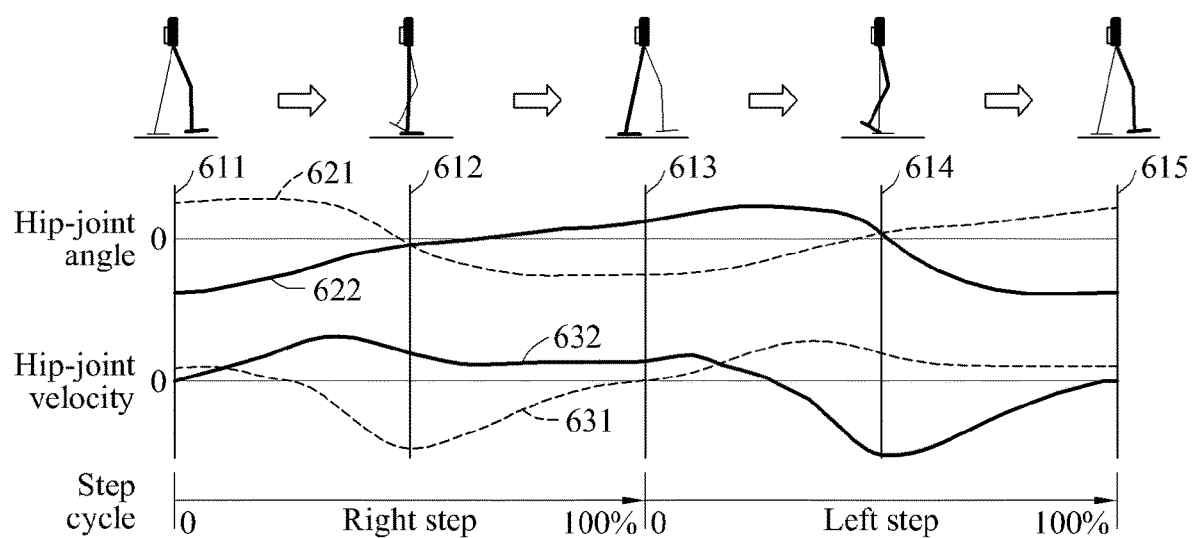
FIG. 6 illustrates an example of setting a basic assisting torque according to example embodiments.

FIG. 6 illustrates an example of setting a basic assisting torque according to example embodiments.

FIG. 6 illustrates a graph indicating a change in gait data during a gait of a user. In the graph of FIG. 6, a horizontal axis represents a time and a vertical axis represents a hip-joint angle or a hip-joint velocity.

A right leg may suspend swinging at a point in time 611. A left leg may swing and intersect the right leg at a point in time 612. The left leg may suspend the swinging at a point in time 613. The right leg may swing and intersect the left leg at a point in time 614. Similarly to the point in time 611, the right leg may suspend the swinging at a point in time 615. For example, a gait motion performed in a period of time from the point in time 611 to the point in time 615 may be a stride, a gait motion performed in a period of time from the point in time 611 to the point in time 613 may be a step of the right leg, and a gait motion performed in a period of time from the point in time 613 to the point in time 615 may be a step of the left leg. A dotted curve 621 may indicate a left hip-joint angle. A solid curve 622 may indicate a right hip-joint angle. A dotted curve 631 may indicate a left hip-joint velocity. A solid curve 632 may indicate a right hip-joint velocity.

In an example, the assisting torque setting apparatus may model a gait state for each of the point in time 611, the point in time 612, the point in time 613, and the point in time 614 in advance. Based on an FSM-based basic assisting torque setting scheme, the assisting torque setting apparatus (e.g., the basic assisting torque setter 230, 440) may apply, to an FSM, both hip-joints angle information indicated by the dotted curve 621 and the solid curve 622 and both hip-joints velocity information indicated by the dotted curve 631 and the solid curve 632, thereby recognizing a gait state corresponding to a gait motion of the user from among four modeled gait states. Through this, the assisting torque setting apparatus may set assisting torques corresponding to the four modeled gait states in advance, and set, as a basic assisting torque, an assisting torque corresponding to the gait state recognized as the gait motion of the user among the four modeled gait states.

In another example, based on an AO-based basic assisting torque setting scheme, the assisting torque setting apparatus (e.g., the basic assisting torque setter 230, 440) may estimate a periodicity, for example, a phase pattern, of the user by applying the both hip-joints angle information and the both hip-joints velocity information to an AO. The assisting torque setting apparatus may set an assisting torque corresponding to each periodicity in advance, and set an assisting torque corresponding to the estimated periodicity as the basic assisting torque setting apparatus.

Figure 7A:
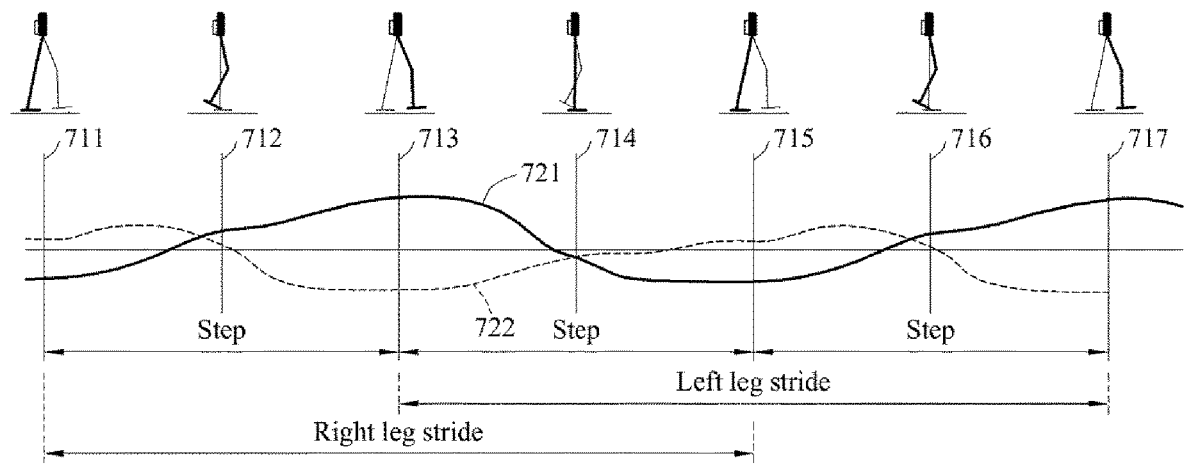
FIGS. 7A and 7B illustrate examples of calculating an evaluation value of a gait symmetry according to example embodiments.
Figure 7B:
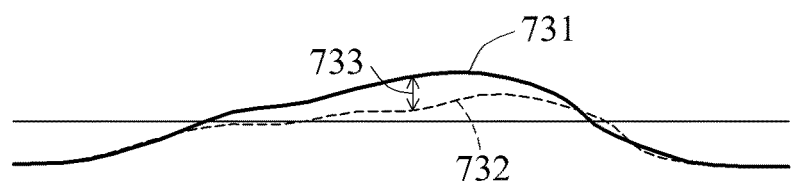

FIGS. 7A and 7B illustrate examples of calculating an evaluation value of a gait symmetry according to example embodiments.

FIG. 7A illustrates a graph indicating a change in a hip-joint angle during a gait of a user. In the graph of FIG. 7A, a horizontal axis represents a time and a vertical axis represents the hip-joint angle.

A left leg may suspend swinging at a point in time 711. A right leg may swing and intersect the left leg at a point in time 712. The right leg may suspend the swinging at a point in time 713. The left leg may swing and intersect the right leg at a point in time 714. The left leg may suspend the swinging at a point in time 715. Also, the right leg may swing and intersect the left leg at a point in time 716, and, similarly to the point in time 713, the right leg may suspend the swinging at a point in time 717. A gait motion performed in a period of time from the point in time 711 to the point in time 715 may be, for example, one stride of the right leg. A gait motion performed in a period of time from the point in time 713 to the point in time 717 may be, for example, one stride of the left leg. Also, each of gait motions performed in a period of time from the point in time 711 to the point in time 713 and a period of time from the point in time 715 to the point in time 717 may be, for example, one step of the left leg. A gait motion performed in a period of time from the point in time 713 to the point in time 715 may be, for example, a step of the right leg. A solid curve 721 may indicate a right hip-joint angle. A dotted curve 722 may indicate a left hip-joint angle.

An assisting torque setting apparatus (e.g., an index evaluator 310, 451) may estimate a similarity between a trajectory, for example, the solid curve 721, of the right hip-joint angle and a trajectory, for example, the dotted curve 722, of the left hip-joint angle. Subsequently, the assisting torque setting apparatus may determine the estimated similarity as an evaluation value of a gait symmetry. The assisting torque setting apparatus may calculate a difference between the trajectory of the right hip-joint angle corresponding to a period of time from the point in time 711 to the point in time 715 and the trajectory of the left hip-joint angle corresponding to a period of time from the point in time 713 to the point in time 717. In this example, the trajectory of the right hip-joint angle corresponding to a period of time from the point in time 711 to the point in time 715 may be spaced apart from the trajectory of the left hip-joint angle corresponding to a period of time from the point in time 713 to the point in time 717 by a single step.

The graph of FIG. 7B indicates a difference 733 between a trajectory 731, as indicated by a solid curve, of the right hip-joint angle corresponding to the period of time from the point in time 711 to the point in time 715 and a trajectory 732, as indicated by a dotted curve, of the left hip-joint angle corresponding to the period of time from the point in time 713 to the point in time 717. In the graph, a horizontal axis represents an NST and a vertical axis represents a hip-joint angle.

The assisting torque setting apparatus may calculate an evaluation value of the gait symmetry based on Equation 1. The assisting torque setting apparatus may apply a DTW to the difference 733 between the trajectory 731 and the trajectory 732, estimate a similarity between the trajectory 731 and the trajectory 732, and calculate the estimated similarity to be the evaluation value of the gait symmetry corresponding to the period of time from the point in time 711 to the point in time 717. Also, the assisting torque setting apparatus may compare the evaluation value and a threshold corresponding to the gait symmetry, and determine whether the gait of the user is stable based on the gait symmetry.

Figure 8A:
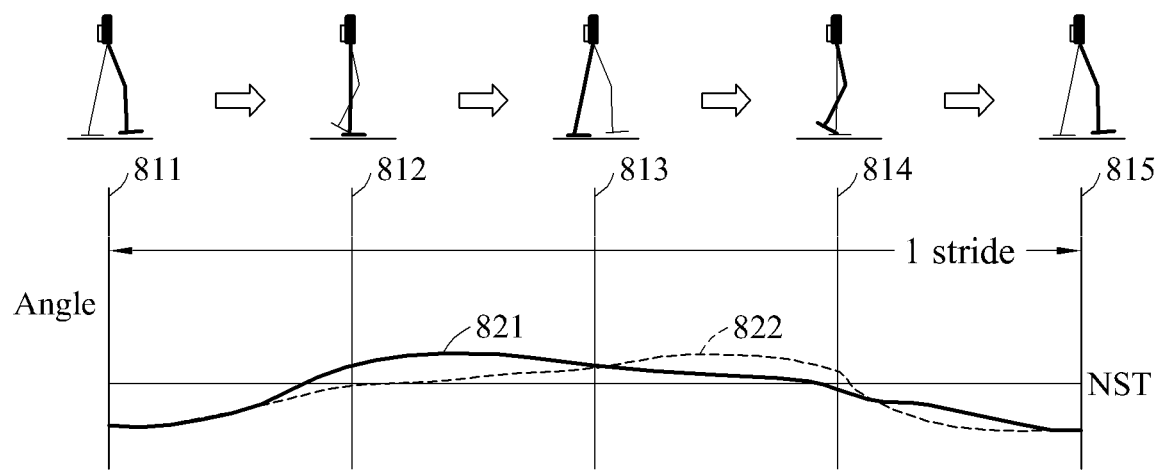
FIGS. 8A and 8B illustrate examples of setting an initial stable assisting torque of a gait symmetry according to example embodiments.
Figure 8B:
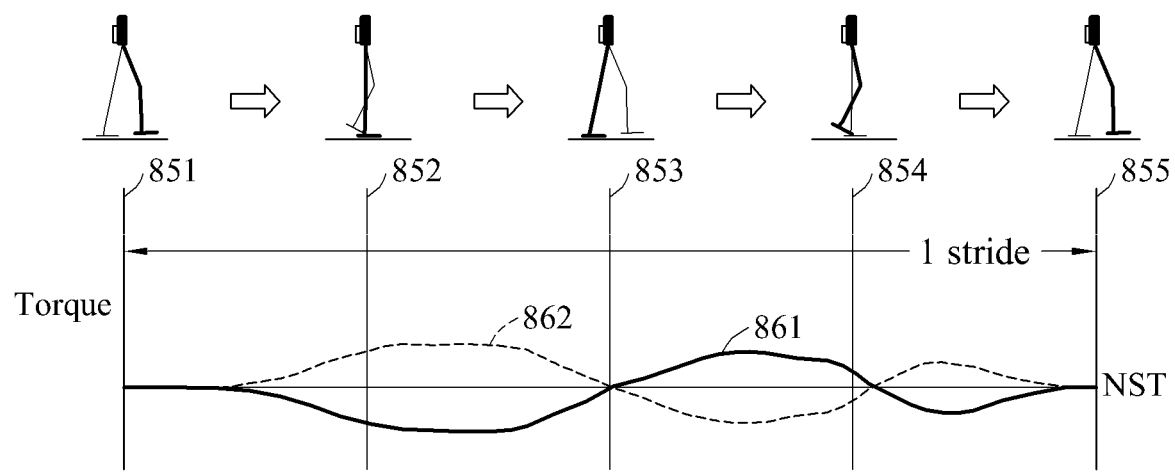

FIGS. 8A and 8B illustrate examples of setting an initial stable assisting torque of a gait symmetry according to example embodiments.

FIG. 8A illustrates a graph indicating a change in a hip-joint angle during a gait of a user. FIG. 8B illustrates a graph indicating an initial stable assisting torque corresponding to the gait of the user. In the graph of FIG. 8A, a horizontal axis represents an NST and a vertical axis represents the hip-joint angle. In the graph of FIG. 8B, a horizontal axis represents an NST and a vertical axis represents the initial stable assisting torque.

A right leg may suspend swinging at a point in time 811. A left leg may swing and intersect the right leg at a point in time 812. The left leg may suspend the swinging at a point in time 813. The right leg may swing and intersect the left leg at a point in time 814. Similarly to the point in time 811, the right leg may suspend the swinging at a point in time 815. A gait motion performed in a period of time from the point in time 811 to the point in time 815 may be a stride, a gait motion performed in a period of time from the point in time 811 to the point in time 813 may be a step of the right leg, and a gait motion performed in a period of time from the point in time 813 to the point in time 815 may be a step of the left leg.

In the graph of FIG. 8A, a solid curve 821 may indicate a right hip-joint angle, and a dotted curve 822 may indicate a left hip-joint angle. In the graph of FIG. 8B, a dotted curve 862 may indicate an initial stable assisting torque provided to a left leg, and a solid curve 861 may indicate an initial stable assisting torque provided to a right leg.

Based on Equations 5 through 7, an assisting torque setting apparatus (e.g., the stable assisting torque setter 220, 453) may set the initial stable assisting torque by multiplying a desired (or, alternatively, predetermined) gain to a difference between a trajectory, for example, the solid curve 821, of the right hip-joint angle and a trajectory, for example, the dotted curve 822, of the left hip-joint angle. To set an initial stable assisting torque, for example, the dotted curve 861, provided to a right leg, the assisting torque setting apparatus may multiply a gain of the initial stable assisting torque provided to the right leg, to a value obtained by subtracting the trajectory of the right hip-joint angle from the trajectory of the left hip-joint angle. Also, set an initial stable assisting torque, for example, the solid curve 862, provided to a left leg, the assisting torque setting apparatus may multiply a gain of the initial stable assisting torque provided to the left leg, to a value obtained by subtracting the trajectory of the left hip-joint angle from the trajectory of the right hip-joint angle.

The initial stable assisting torque for the right leg may be applied to a time, starting from the point in time 811, and the initial stable assisting torque for the left leg may be applied to a time, starting from the point in time 813.

Through this, the assisting torque setting apparatus may set the initial stable assisting torque provided to the left leg and the initial stable assisting torque provided to the right leg thereby offsetting the difference between the trajectory of the left hip-joint angle and the trajectory of the right hip-joint angle.

Figure 9:
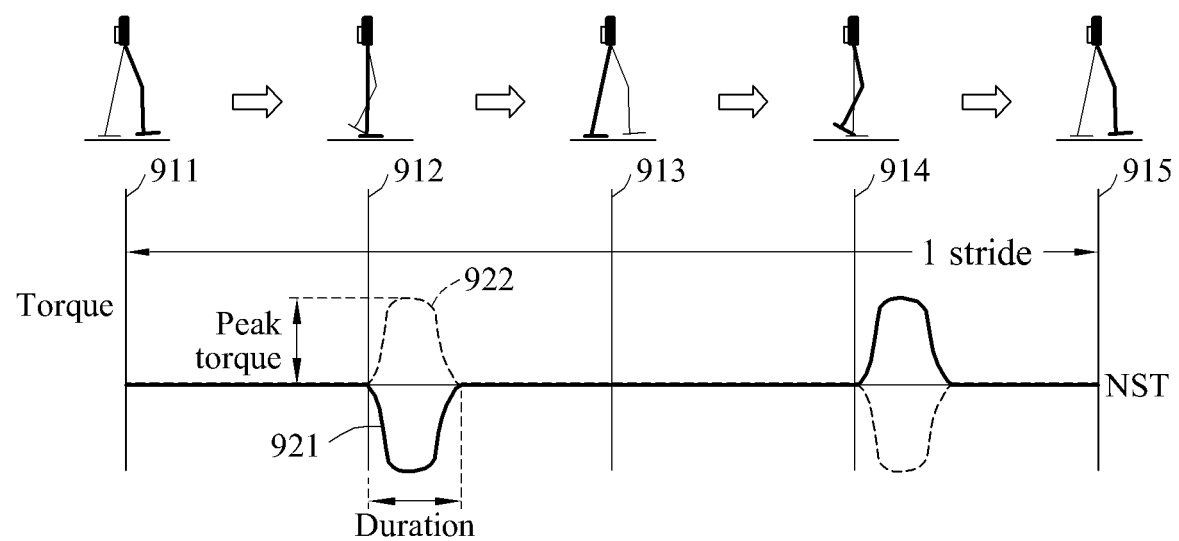
FIG. 9 illustrates an example of setting an initial stable assisting torque of a stride length according to example embodiments.

FIG. 9 illustrates an example of setting an initial stable assisting torque of a stride length according to example embodiments.

FIG. 9 illustrates a graph indicating an initial stable assisting torque corresponding to a gait of a user. In the graph of FIG. 9, a horizontal axis represents an NST and a vertical axis represents the initial stable assisting torque.

A right leg may suspend swinging at a point in time 911. A left leg may swing and intersect the right leg at a point in time 912. The left leg may suspend the swinging at a point in time 913. The right leg may swing and intersect the left leg at a point in time 914. Similarly to the point in time 911, the right leg may suspend the swinging at a point in time 915. For example, a gait motion performed in a period of time from the point in time 911 to the point in time 915 may be a stride, a gait motion performed in a period of time from the point in time 911 to the point in time 913 may be a step of the right leg, and a gait motion performed in a period of time from the point in time 913 to the point in time 915 may be a step of the left leg. In the graph, a solid curve 921 may indicate an initial stable assisting torque provided to a right leg, and a dotted curve 922 may indicate an initial stable assisting torque provided to a left leg.

Based on Equation 8, a assisting torque setting apparatus (e.g., the assisting torque setter 330 or the stable assisting torque determiner 453) may extract an intersecting point in time between the left leg and the right leg using a trajectory of a left hip-joint angle and a trajectory of a right hip-joint angle, and set a peak torque of a desired (or, alternatively a predetermined) period of time from the intersecting point in time, as an initial stable assisting torque of a stride length. In this example, the period of time and the peak torque may be set in advance. In an example of FIG. 9, the assisting torque setting apparatus may extract each of a point in time 912 and a point in time 914 as the intersecting point in time between the left leg and the right leg. The assisting torque setting apparatus may set the initial stable assisting torque, for example, the dotted curve 921, provided to the right leg and the initial stable assisting torque, for example, the solid curve 922, provided to the left leg such that the peak torque is provided to the left leg and the right leg during the period of time from the point in time 912 to the point in time 914. Through this, the assisting torque setting apparatus may set the initial stable assisting torque provided to the left leg and the initial stable assisting torque provided to the right leg such that the left leg and the right leg are spaced apart from one another during the period of time from the point in time 912 to the point in time 914.

Figure 10:
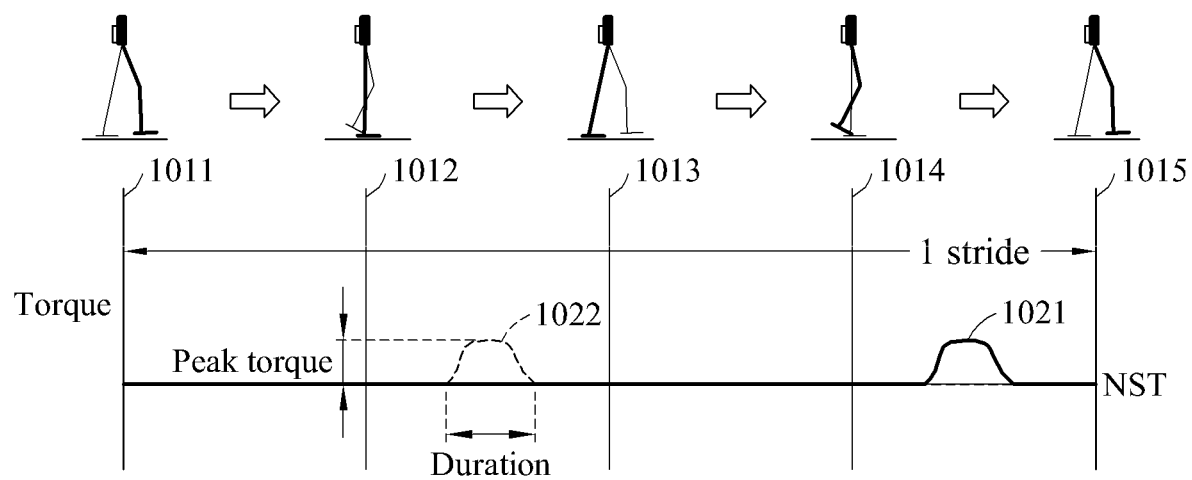
FIG. 10 illustrates an example of setting an initial stable assisting torque of a foot clearance according to example embodiments.

FIG. 10 illustrates an example of setting an initial stable assisting torque for a foot clearance according to example embodiments.

FIG. 10 illustrates a graph indicating an initial stable assisting torque corresponding to a gait of a user. In the graph of FIG. 10, a horizontal axis represents an NST and a vertical axis represents the initial stable assisting torque.

A right leg may suspend swinging at a point in time 1011. A left leg may swing and intersect the right leg at a point in time 1012. The left leg may suspend the swinging at a point in time 1013. The right leg may swing and intersect the left leg at a point in time 1014. Similarly to the point in time 1011, swinging of the right leg may be suspended at a point in time 1015. A gait motion performed in a period of time from the point in time 1011 to the point in time 1015 may be a stride, a gait motion performed in a period of time from the point in time 1011 to the point in time 1013 may be a step of the right leg, and a gait motion performed in a period of time from the point in time 1013 to the point in time 1015 may be a step of the left leg. In the graph, a solid curve 1021 may indicate an initial stable assisting torque provided to a right leg, and a dotted curve 1022 may indicate an initial stable assisting torque provided to a left leg.

Based on Equation 9, an assisting torque setting apparatus may extract a point in time at which a swinging leg of the user approaches a ground, based on a trajectory of a left hip-joint angle and a trajectory of a right hip-joint angle, and set a peak torque of a desired (or, alternatively, predetermined) period of time from the extracted point in time, as the initial stable assisting torque of the foot clearance. In this example, the period of time and the peak torque may be set in advance. In an example of FIG. 10, the assisting torque setting apparatus may extract a point in time between the point in time 1012 and the point in time 1013, as a point in time at which the left leg approaches the ground, and extract a point in time between the point in time 1014 and the point in time 1015, as a point in time at which the right leg approaches the ground.

The assisting torque setting apparatus may set the initial stable assisting torque, for example, the dotted curve 1022, provided to the left leg such that the peak torque is provided to the left leg during a desired (or, alternatively, predetermined) period of time from the point in time between the point in time 1012 and the point in time 1013. Also, the assisting torque setting apparatus may set the initial stable assisting torque, for example, the solid curve 1021, provided to the right leg such that the peak torque is provided to the right leg during a desired (or, alternatively, predetermined) period of time from the point in time between the point in time 1014 and the point in time 1015. Through this, the assisting torque setting apparatus may set the initial stable assisting torque for the left leg such that the left leg is lifted to an increased height during the period of time from the point in time between the point in time 1012 and the point in time 1013, and may set the initial stable assisting torque for the right leg such that the right leg is lifted to an increased height during the period of time from the point in time between the point in time 1014 and the point in time 1015.

Figure 11:
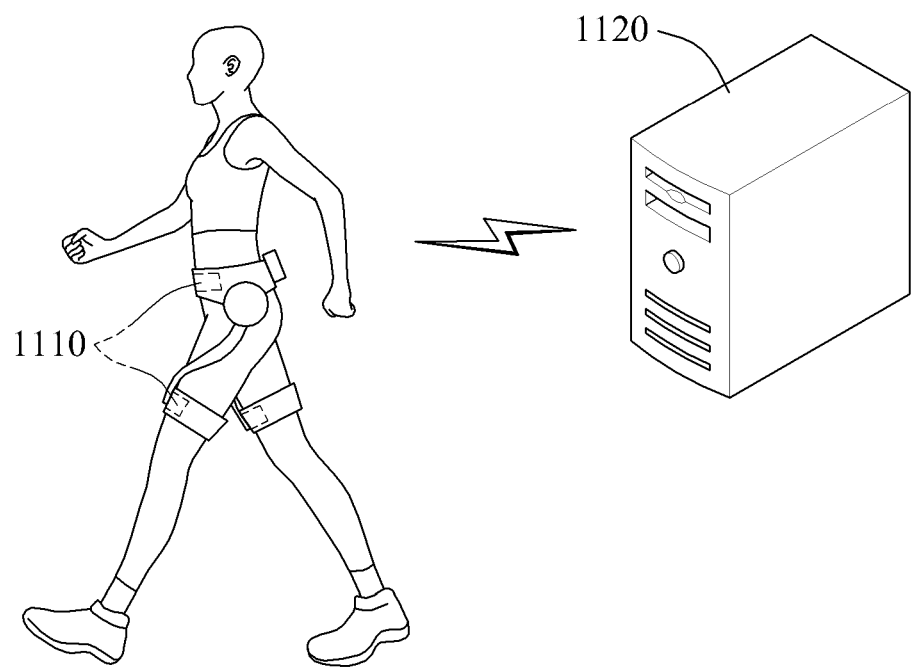
FIG. 11 illustrates an example of setting an assisting torque according to example embodiments.

FIG. 11 illustrates an example of setting an assisting torque according to example embodiments.

Referring to FIG. 11, an assisting torque setting apparatus may be included in a walking assistance apparatus 1110 and/or an external apparatus 1120, for example, a server.

In an example, when the assisting torque setting apparatus is included in the walking assistance apparatus 1110, the assisting torque setting apparatus may receive, from a sensor included in the walking assistance apparatus 1110, gait data obtained by sensing a change in an amount of exercise performed by a user based on a gait motion. The assisting torque sensing apparatus may calculate an evaluation value of at least one index based on the gait data, and calculate a weight of the at least one index based on a difference between the evaluation value and a threshold corresponding to the at least one index. In this example, the assisting torque setting apparatus may receive information associated with the threshold corresponding to the at least one index from the external apparatus 1120 through a communication interface. Also, the assisting torque setting apparatus may set an initial stable assisting torque corresponding to the at least one index based on the gait data, and set a stable assisting torque by applying the weight to the initial stable assisting torque. The assisting torque setting apparatus may set a basic assisting torque based on the gait data, and set a final assisting torque by combining the basic assisting torque and the stable assisting torque. The assisting torque setting apparatus may control the walking assistance apparatus 1110 to output the final assisting torque. Also, the assisting torque setting apparatus may transmit the gait data of the user, the evaluation value of the at least one index, the weight, the initial stable assisting torque, the basic assisting torque, and the final assisting torque, to the external apparatus 1120 through the communication interface.

In another example, when the assisting torque setting apparatus is included in the external apparatus 1120, the assisting torque setting apparatus may receive, from the walking assistance apparatus 1110, gait data obtained by a sensor included in the walking assistance apparatus 1110 to sense a change in an amount of exercises of a user based on a gait motion. The assisting torque sensing apparatus may calculate an evaluation value of at least one index based on the received gait data, and calculate a weight of the at least one index based on a difference between the evaluation value and a threshold corresponding to the at least one index. In this example, the threshold corresponding to the at least one index may be set in advance. Also, the assisting torque setting apparatus may set an initial stable assisting torque corresponding to the at least one index based on the gait data, and set a stable assisting torque by applying the weight to the initial stable assisting torque. The assisting torque setting apparatus may set a basic assisting torque based on the gait data, and set a final assisting torque by combining the basic assisting torque and the stable assisting torque. The assisting torque setting apparatus may control the walking assistance apparatus 1110 to output the final assisting torque. Also, the assisting torque setting apparatus may transmit a control signal to the walking assistance apparatus 1110 through the communication interface such that the walking assistance apparatus 1110 is driven based on the final assisting torque. The walking assistance apparatus 1110 may output the final assisting torque based on the control signal.

Figure 12:
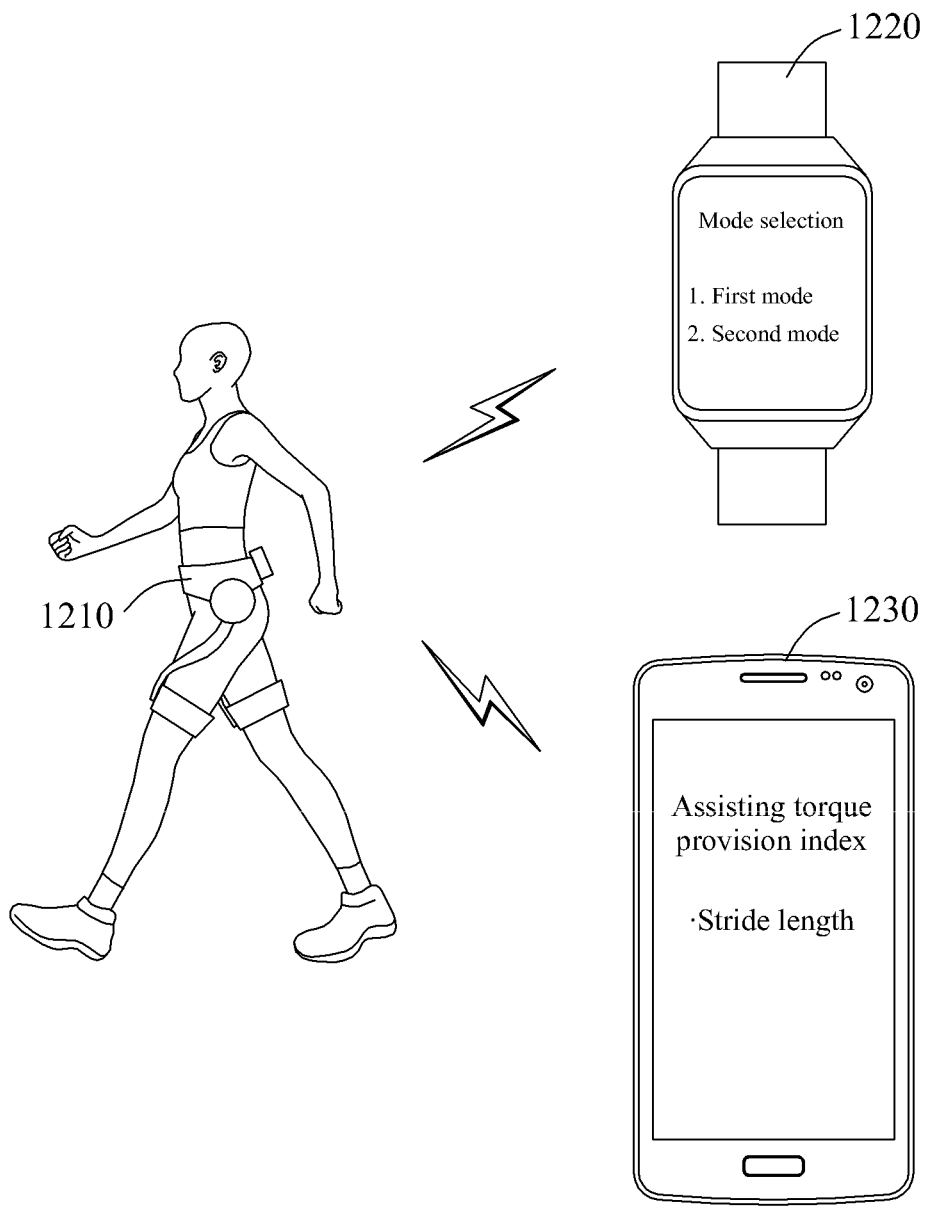
FIG. 12 illustrates an example of an interface for providing an assisting torque according to example embodiments.

FIG. 12 illustrates an example of an interface for providing an assisting torque according to example embodiments.

Referring to FIG. 12, a walking assistance apparatus 1210 may receive an operation mode selected by a wearable device 1220 and/or a mobile device 1230 through a communication interface.

In an example, the operation mode may include a first operation mode and a second operation mode. The first operation mode may be an operation mode in which the walking assistance apparatus 1210 provides an assistance torque for a gait to a user. The second operation mode may be an operation mode in which the walking assistance apparatus 1210 provides an assisting torque to a user to prevent an accidental fall of the user.

As an example, when the first operation mode is selected, the assistance torque for preventing the accidental fall may not be applied. As another example, when the second operation mode is selected, the walking assistance apparatus 1210 may calculate a final assistance torque to which the assistance torque for the gait and the assistance torque for preventing the accidental fall are applied. In another example, the walking assistance apparatus 1210 may receive, from a sensor (not shown), gait data obtained by sensing a change in an amount of exercise of a user based on a gait motion. The sensor may be connected to the walking assistance apparatus 1210 through a wired communication and a wireless communication.

The walking assistance apparatus 1210 may calculate an evaluation value of an index based on the gait data. The walking assistance apparatus 1210 may calculate a weight of the index based on a difference between the evaluation value and a threshold corresponding to the index. The walking assistance apparatus 1210 may set an initial stable assisting torque corresponding to the index based on the gait data, and set a stable assisting torque by applying the weight to the initial stable assisting torque. The walking assistance apparatus 1210 may set a basic assisting torque based on the gait data, and set a final assisting torque by combining the basic assisting torque and the stable assisting torque. The walking assistance apparatus 1210 may output the final assisting torque set when the first operation mode is selected.

In still another example, the walking assistance apparatus 1210 may transmit information on the evaluation value of the index, the weight, the initial stable assisting torque, the basic assisting torque, and the final assisting torque, to the wearable device 1220 or the mobile device 1230 through the communication interface. The wearable device 1220 or the mobile device 1230 may display the information received from the walking assistance apparatus 1210. For example, as illustrated in FIG. 12, the wearable device 1220 or the mobile device 1230 may display information indicating that an index about a stride length is applied to set the final assisting torque.

Figure 13:
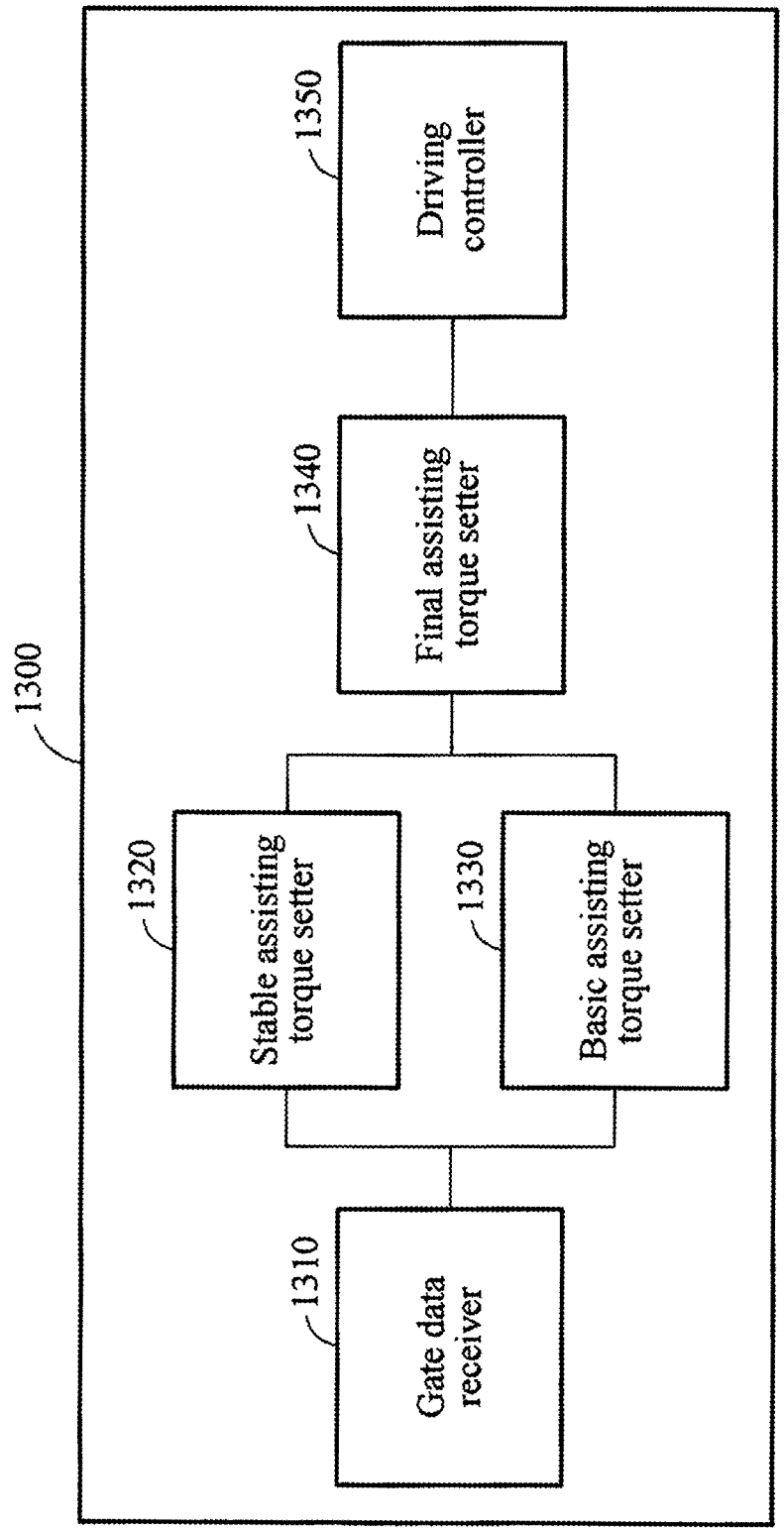
FIG. 13 illustrates another example of a walking assistance apparatus according to example embodiments.

FIG. 13 illustrates a walking assistance apparatus according to example embodiments.

Referring to FIG. 13, the walking assistance apparatus 1300 includes a gait data receiver 1310, a stable assisting torque setter 1320, a basic assisting torque setter 1330, a final assisting torque setter 1340, and a driving controller 1350.

The gait data receiver 1310 may receive gait data of a user.

The stable assisting torque setter 1320 may set a stable assisting torque using an evaluation value of at least one index calculated based on the gait data.

The basic assisting torque setter 1330 may set a basic assisting torque corresponding to a gait motion of the user based on the gait data.

The final assisting torque setter 1340 may set a final assisting torque based on the stable assisting torque and the basic assisting torque.

Since the descriptions provided with reference to the gait data receiver 210, the stable assisting torque setter 220, the basic assisting torque setter 230, and the final assisting torque setter 240 of FIG. 2 are also applicable here, repeated descriptions with respect to the gait data receiver 1310, the stable assisting torque setter 1320, the basic assisting torque setter 1330, and the final assisting torque setter 1340 of FIG. 13 will be omitted for increased clarity and conciseness.

The driving controller 1350 may control driving of the walking assistance apparatus 1300 based on the final assisting torque. In an example, the walking assistance apparatus 1300 may include the driving portion 110 configured to drive both hip-joints of the user, and control the driving portion 110 to output the final assisting torque. For example, the driving controller 1350 may transmit a control signal to the driving portion 110 to output a gain corresponding to the final assisting torque. In this example, the driving portion 110 may output the gain corresponding to the final assisting torque based on the control signal. Accordingly, the walking assistance apparatus 1300 may assist the user to stably perform a gait based on the final assisting torque, thereby protecting the user from a falling accident.

Figure 14:
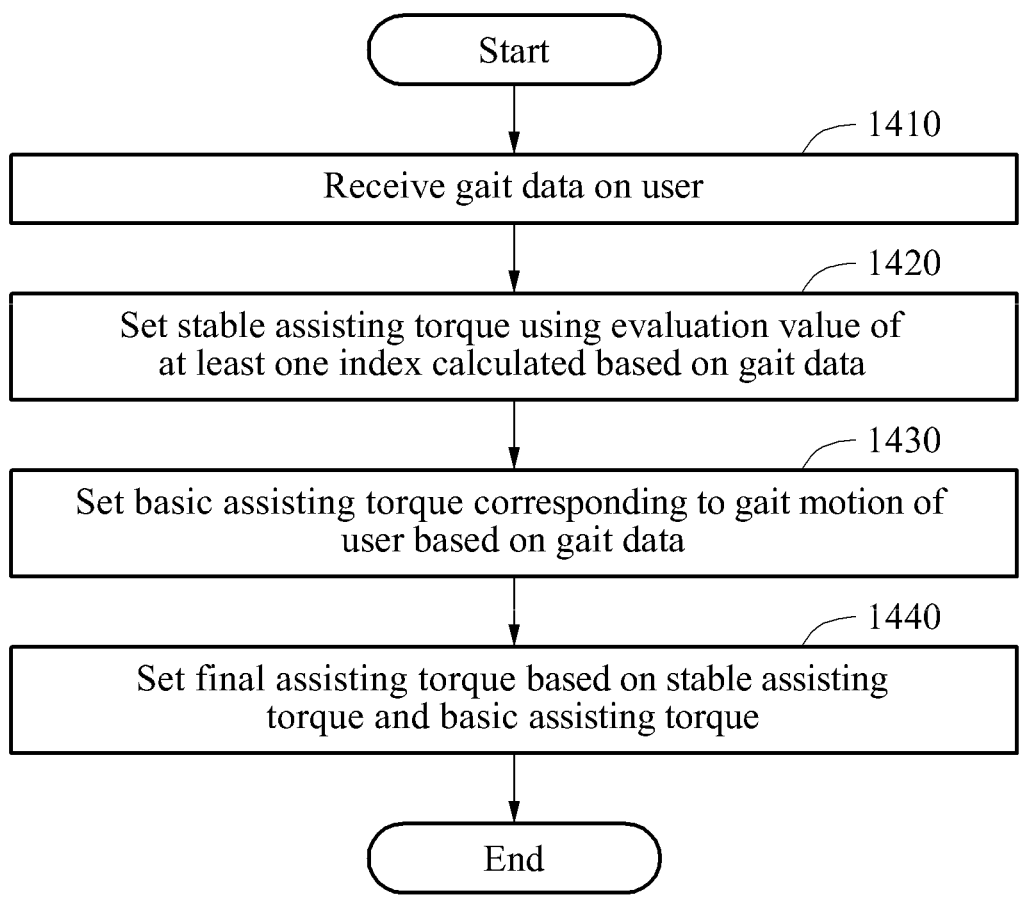
FIG. 14 illustrates an example of an assisting torque setting method according to example embodiments.

FIG. 14 illustrates an example of an assisting torque setting method according to example embodiments.

Referring to FIG. 14, in operation 1410, an assisting torque setting apparatus receives gait data of a user.

In operation 1420, the assisting torque setting apparatus sets a stable assisting torque using an evaluation value of at least one index calculated based on the gait data.

In operation 1430, the assisting torque setting apparatus sets a basic assisting torque corresponding to a gait motion of the user based on the gait data.

In operation 1440, the assisting torque setting apparatus sets a final assisting torque based on the stable assisting torque and the basic assisting torque.

Since the descriptions provided with reference to FIGS. 1A through 13 are also applicable here, repeated descriptions with respect to the assisting torque setting method of FIG. 14 will be omitted for increased clarity and conciseness.

Figure 15:
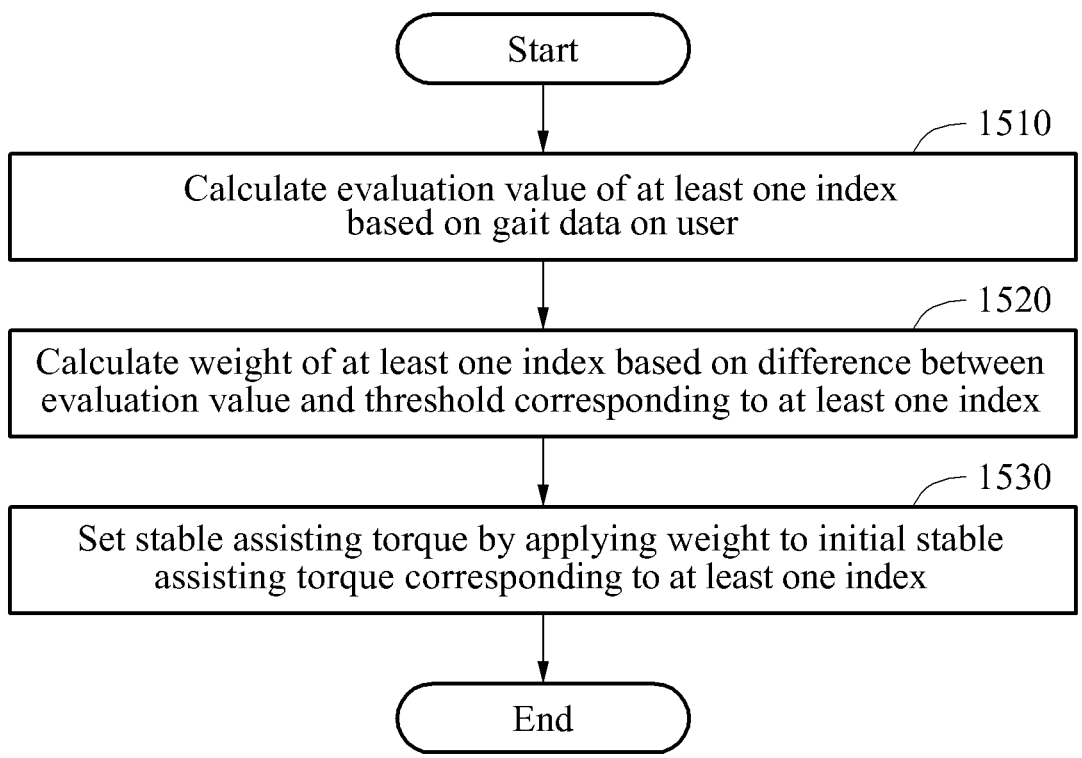
FIG. 15 illustrates another example of an assisting torque setting method according to example embodiments.

FIG. 15 illustrates another example of an assisting torque setting method according to example embodiments.

Referring to FIG. 15, in operation 1510, an assisting torque setting apparatus calculates an evaluation value of at least one index indicating a gait stability of a user based on gait data of the user.

In operation 1520, the assisting torque setting apparatus calculates a weight of the at least one index based on a difference between the evaluation value and a threshold corresponding to the at least one index.

In operation 1530, the assisting torque setting apparatus sets a stable assisting torque by applying the weight to an initial stable assisting torque corresponding to the at least one index.

Since the descriptions provided with reference to FIGS. 1A through 13 are also applicable here, repeated descriptions with respect to the assisting torque setting method of FIG. 15 will be omitted for increased clarity and conciseness.

Figure 16:
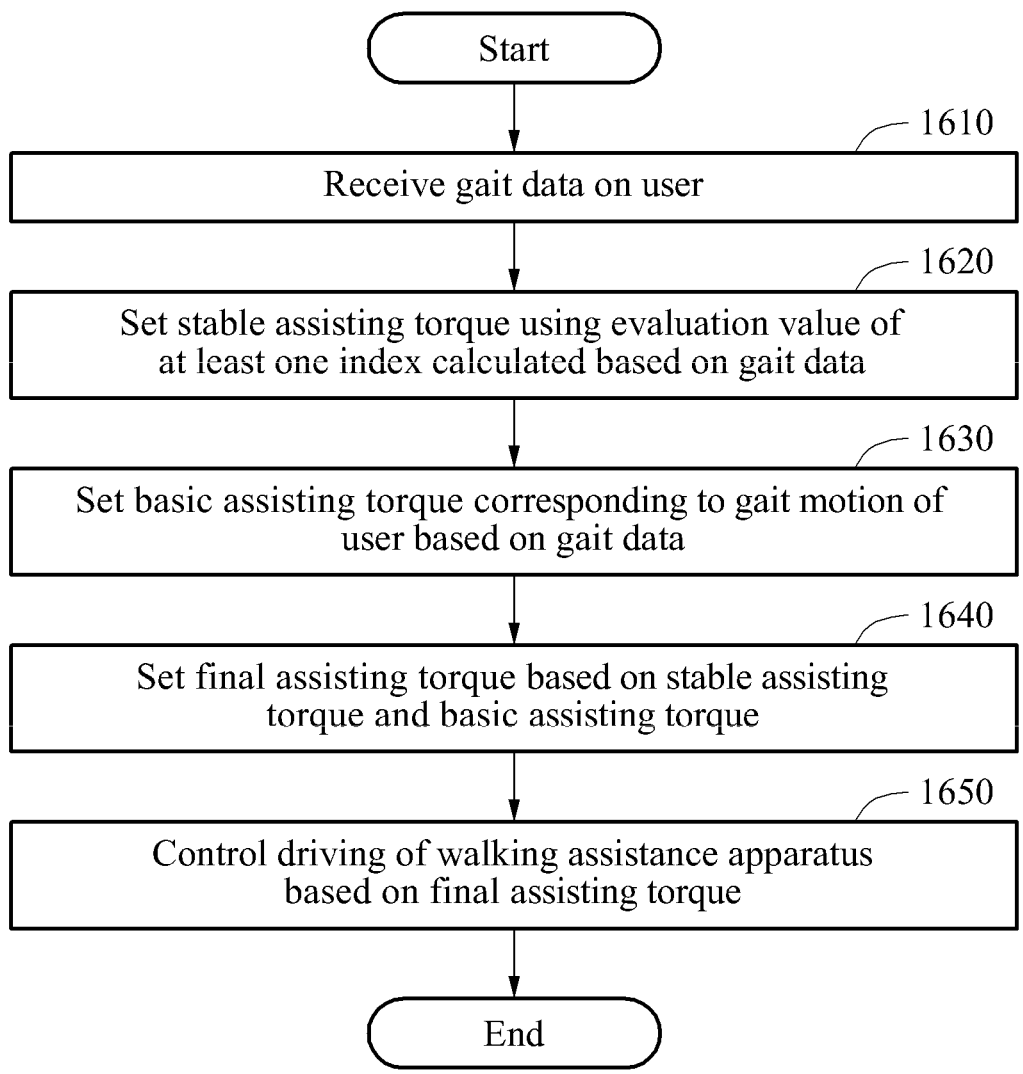
FIG. 16 illustrates an example of a walking assistance method according to example embodiments.

FIG. 16 illustrates an example of a walking assistance method according to example embodiments.

Referring to FIG. 16, in operation 1610, a walking assistance apparatus receives gait data of a user.

In operation 1620, the walking assistance apparatus sets a stable assisting torque using an evaluation value of at least one index calculated based on the gait data.

In operation 1630, the walking assistance apparatus sets a basic assisting torque corresponding to a gait motion of the user based on the gait data.

In operation 1640, the walking assistance apparatus sets a final assisting torque based on the stable assisting torque and the basic assisting torque.

In operation 1650, the walking assistance apparatus controls driving of the walking assistance apparatus based on the final assisting torque.

Since the descriptions provided with reference to FIGS. 1A through 13 are also applicable here, repeated descriptions with respect to the walking assistance method of FIG. 16 will be omitted for increased clarity and conciseness.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

Figure 17:
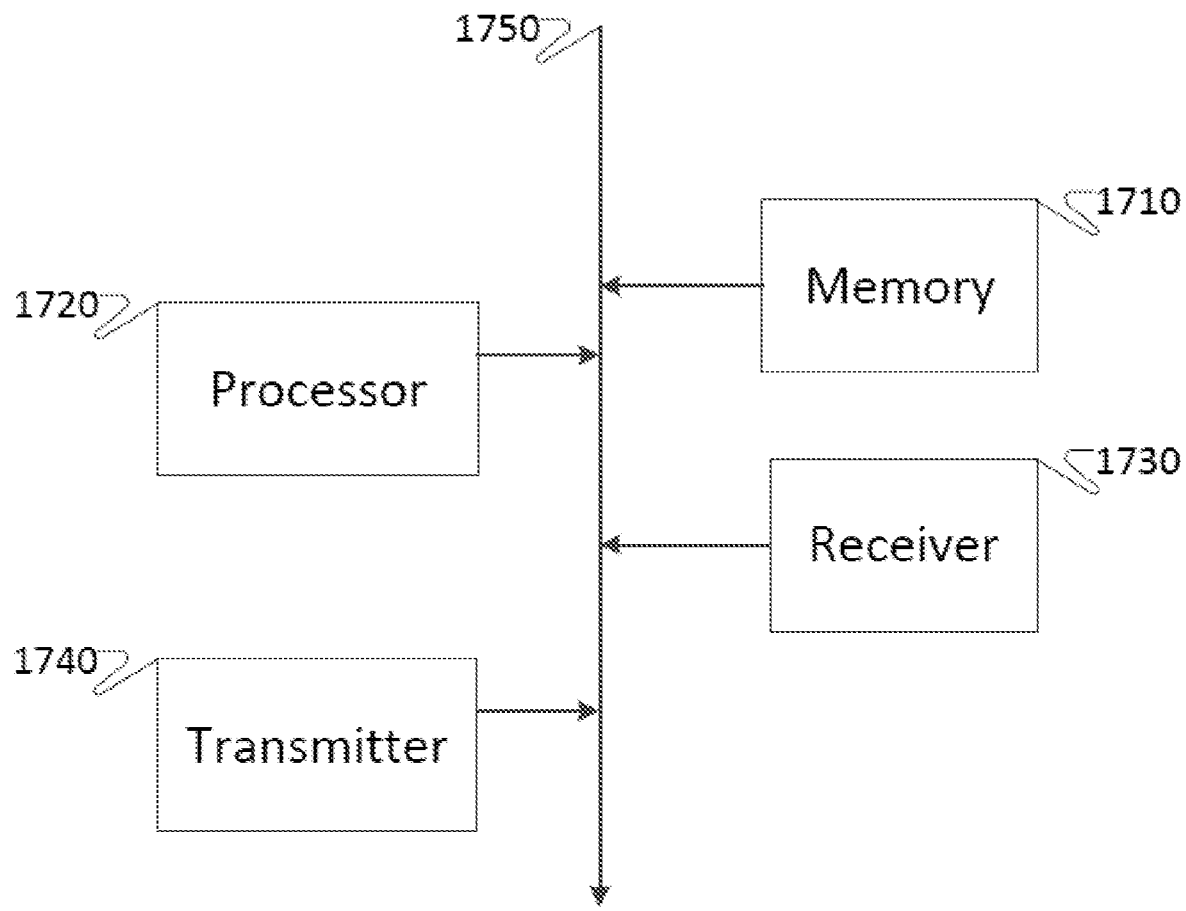
FIG. 17 illustrates a controller according to some example embodiments.

FIG. 17 illustrates a controller according to some example embodiments.

Referring to FIG. 17, the controller 140 and/or server 1120 may include memory 1710, a processor 1720, a receiver 1730 and a transmitter 1740 that may send data to and/or receive data from one another using a data bus 1750.

The memory 1710 may be any device capable of storing data. For example, the memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The receiver 1730 and transmitter 1740 may transmit and receive signals, for example, from the driving portion 110, the sensing portion and/or the controller 140.

The processor 1720 may be any device capable of processing data including, for example, a microprocessor configured to carry out specific operations by performing arithmetical, logical, and input/output operations based on input data, or capable of executing instructions included in computer readable code. The processor 1720 may be a logic chip, for example, a central processing unit (CPU), a controller, or an application-specific integrated circuit (ASIC), that when, executing the instructions stored in the memory 1710, configures the processor 1720 as a special purpose machine such that the processor 720 is configured to determine whether the gait motion associated with the user is stable based on whether evaluation values of the gait motion are less than or equal to threshold values associated therewith, and selectively apply only a basic assistance torque to a user thereof or whether to incorporate a stable assistance torque, depending on whether the gait motion is determined to be unstable.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An assisting torque setting apparatus comprising:
a receiver configured to receive gait data of a user; and
a processor and a memory, the memory containing computer readable code that, when executed by the processor, configures the processor as,
a stable assisting torque setter configured to set a stable assisting torque using an evaluation value of at least one index calculated based on the gait data by being configured at least as an index evaluator configured to classify the gait data based on a stride and to calculate the evaluation value of the at least one index based on the classified gait data,
a basic assisting torque setter configured to set a basic assisting torque corresponding to a gait motion of the user calculated based on the gait data, and
a final assisting torque setter configured to set a final assisting torque based on the stable assisting torque and the basic assisting torque.

2. The assisting torque setting apparatus of claim 1, wherein, when performing functions of the stable assisting torque setter, the processor is further configured as,
a weight calculator configured to calculate a weight of the at least one index based on a difference between the evaluation value and a threshold corresponding to the at least one index; and
a stable assisting torque calculator configured to calculate the stable assisting torque by applying the weight to an initial stable assisting torque corresponding to the at least one index.

3. The assisting torque setting apparatus of claim 2, wherein the at least one index comprises at least one of a gait symmetry indicating a degree of symmetry between both legs of the user, a stride length of the user, a stride width of the user, a foot clearance indicating a space between a ground and a foot of the user, a landing speed indicating a speed of the foot descending to the ground, and a walk ratio.

4. The assisting torque setting apparatus of claim 3, wherein, when performing functions of the index evaluator, the processor is configured to compare the evaluation value to the threshold corresponding to the at least one index, and to determine whether a gait of the user is stable based on the at least one index.

5. The assisting torque setting apparatus of claim 4, wherein, when performing functions of the weight calculator, the processor is configured to set "0" as a weight of the at least one index in which the gait of the user is stable.

6. The assisting torque setting apparatus of claim 3, wherein, when performing functions of the index evaluator, the processor is configured to estimate a similarity between a trajectory of a left hip joint angle and a trajectory of a right hip-joint angle of the user in the gait data, and determine the similarity as an evaluation value of the gait symmetry.

7. The assisting torque setting apparatus of claim 6, wherein the index evaluator is configured to estimate the similarity between the trajectory of the left hip joint angle and the trajectory of the right hip joint angle of the user based on a dynamic time warping (DTW).

8. The assisting torque setting apparatus of claim 3, wherein, when performing functions of the index evaluator, the processor is configured to estimate, with respect to a plurality of strides, an average stride length by calculating an average of a left hip-joint angle range and a right hip-joint angle range in the gait data, and to determine the average stride length as an evaluation value of the stride length.

9. The assisting torque setting apparatus of claim 3, wherein, when performing functions of the index evaluator, the processor is configured to,
extract, with respect to a plurality of strides, a maximum flexion angle of a left hip-joint and a maximum flexion angle of a right hip joint from the gait data, and
determine the maximum flexion angle of the left hip joint and the maximum flexion angle of the right hip-joint as an evaluation value of the foot clearance.

10. The assisting torque setting apparatus of claim 3, wherein, when performing functions of the stable assisting torque calculator, the processor is configured to set the initial stable assisting torque based on the gait data.

11. The assisting torque setting apparatus of claim 10, wherein, when performing functions of the stable assisting torque calculator, the processor is configured to set the initial stable assisting torque for the gait symmetry based on a difference between a trajectory of a left hip joint angle and a trajectory of a right hip-joint angle in the gait data.

12. The assisting torque setting apparatus of claim 11, wherein, when performing functions of the stable assisting torque calculator, the processor is configured to,
   extract an intersecting point in time at which a left leg and a right leg of the user intersect, based on the trajectory of the left hip joint angle and the trajectory of the right hip joint angle in the gait data, and
   set a peak torque of a period of time from the intersecting point in time as the initial stable assisting torque of the stride length.

13. The assisting torque setting apparatus of claim 11, wherein, when performing functions of the stable assisting torque calculator, the processor is configured to,
   extract a point in time at which a swinging leg of the user approaches a ground based on the trajectory of the left hip joint angle and the trajectory of the right hip joint angle in the gait data, and
   set a peak torque of a predetermined period of time from the extracted point in time as the initial stable assisting torque of the foot clearance.

14. The assisting torque setting apparatus of claim 2, wherein, when performing functions of the weight calculator, the processor is configured to calculate the weight by normalizing the difference between the evaluation value and the threshold.

15. The assisting torque setting apparatus of claim 1, wherein
   the processor is further configured to perform functions of a gait motion recognizer configured to recognize the gait motion of the user based on the gait data, and
   when performing functions of the basic assisting torque setter, the processor is configured to set the basic assisting torque as "0" in response to recognizing that the user does not perform the gait motion.

16. The assisting torque setting apparatus of claim 1, wherein, when performing functions of the basic assisting torque setter, the processor is configured to,
   estimate a periodicity of the gait motion of the user by applying the gait data to an adaptive oscillator (AO), and
   set an assisting torque corresponding to the estimated periodicity as the basic assisting torque.

17. The assisting torque setting apparatus of claim 1, wherein, when performing functions of the basic assisting torque setter, the processor is configured to,
   model the gait motion of the user to be in a plurality of states,
   recognize a gait state corresponding to the gait motion of the user among the plurality of states by applying the gait data to a finite state machine (FSM), and
   set an assisting torque obtained based on the recognized gait state as the basic assisting torque.

18. The assisting torque setting apparatus of claim 1, wherein, when performing functions of the final assisting torque setter, the processor is configured to set the final assisting torque by combining the stable assisting torque and the basic assisting torque.

19. The assisting torque setting apparatus of claim 1, wherein, when performing functions of the final assisting torque setter, the processor is configured to set a value having a greater absolute value between the stable assisting torque and the basic assisting torque, as the final assisting torque.

20. An assisting torque setting apparatus comprising:
   a memory and a processor, the memory containing computer readable code that, when executed by the processor, configures the processor to,
   classify gait data of a user based on a stride,
   calculate an evaluation value of at least one index indicating a gait stability of a user based on the classified gait data of the user,
   calculate a weight of the at least one index based on a difference between the evaluation value and a threshold corresponding to the at least one index, and
   set a stable assisting torque by applying the weight to an initial stable assisting torque corresponding to the at least one index.

21. A walking assistance apparatus comprising:
   a receiver configured to receive gait data of a user; and
   a memory and a processor, the memory containing computer readable code that, when executed by the processor, configures the processor to,
   classify the gait data based on a stride,
   calculate an evaluation value of at least one index based on the classified gait data,
   set a stable assisting torque based on the evaluation value,
   set a basic assisting torque corresponding to a gait motion of the user based on the gait data,
   set a final assisting torque based on the stable assisting torque and the basic assisting torque, and
   control driving of the walking assistance apparatus based on the final assisting torque.

22. A walking assistance apparatus comprising:
   an assistance device configured to be worn on legs of a user;
   a driver configured to output a final assistance torque to drive the assistance device; and
   a controller configured to determine the final assistance torque by,
   determining a basic assistance torque based on a gait motion of the user from gait data,
   determining a stable assistance torque by classifying gait data based on a stride, calculating an evaluation value of at least one index based on the classified gait data, and determining the stable assistance torque based on the evaluation values, and
   determining the final assistance torque based on one or more of the stable assistance torque and the basic assistance torque.

23. The walking assistance apparatus of claim 22, wherein the basic assistance torque is not a function of the evaluation values.

24. The walking assistance apparatus of claim 23, wherein the gait motion is one of a step of one of the legs of the user and a stride of the legs of the user.

25. The walking assistance apparatus of claim 23, wherein the controller is configured to,
   evaluate the gait motion to generate the evaluation values by determining one or more of a symmetry between the gait motion of a right leg of the user and the gait motion of a left leg of the user, a length of a stride included in the gait motion, a width of the stride, a clearance between a foot of the user and a ground, a speed in which the foot of the user contacts the ground, and a number of strides in the gait motion in a period of time, and
   determine whether the gait motion is stable based on whether the evaluation values less than or equal to threshold values associated therewith.

26. The walking assistance apparatus of claim 25, wherein the controller is configured to set the basic assistance torque as the final assistance torque, if the controller determines that the gait motion is stable.

27. The walking assistance apparatus of claim 25, wherein the controller is configured to,
- correct a difference between trajectories of the legs of the user based on an initial assistance torque associated with the symmetry, and
- set a time period in which the initial assistance torque is provided to each of the legs of the user based on the length of the stride, and set a peak torque associated with the initial assistance torque based on a time at which the clearance is smallest.

28. The walking assistance apparatus of claim 25, wherein the controller is configured to,
- determine a weight given to the evaluation values based on a difference between each of the evaluation values and a respective one of the threshold values associated therewith.

29. The walking assistance apparatus of claim 28, wherein the weight given to each of the evaluation values increases as the difference between the evaluation value and the respective one of the threshold values increases.

30. The walking assistance apparatus of claim 28, wherein the controller is configured to,
- determine the stable assistance torque by applying the weight to initial assistance torques associated with each of the evaluation values.

31. The walking assistance apparatus of claim 30, wherein the controller is configured to determine the basic assistance torque by applying the gait motion to one of an adaptive oscillator and a finite state machine.

32. The walking assistance apparatus of claim 31, wherein the controller is configured to determine the basic assistance torque using the adaptive oscillator by estimating a pattern of the gait motion.

33. The walking assistance apparatus of claim 31, wherein the controller is configured to determine the basic assistance torque using the finite state machine by determining which of a plurality of gait states associated with the finite state machine correspond to the gait motion.

34. The walking assistance apparatus of claim 22, further comprising:
- one or more sensors configured to detect information associated with the gait motion of the user.

35. The walking assistance apparatus of claim 34, wherein the information comprises information on one or more of angles of hip joints of the user, a moving direction of the hip joints of the user.

* * * * *